United States Patent
Madan et al.

(10) Patent No.: US 11,278,587 B2
(45) Date of Patent: *Mar. 22, 2022

(54) TREATMENT OF CANCER WITH LARAZOTIDE DERIVATIVES IN COMBINATION WITH IMMUNE CHECKPOINT INHIBITORS

(71) Applicants: 9 METERS BIOPHARMA, INC., Raleigh, NC (US); Institut Gustave Roussy, Villejuif (FR)

(72) Inventors: Jay Madan, Raleigh, NC (US); Sandeep Laumas, Raleigh, NC (US)

(73) Assignee: 9 METERS BIOPHARMA, INC., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/239,056

(22) Filed: Apr. 23, 2021

(65) Prior Publication Data
US 2021/0236586 A1    Aug. 5, 2021

Related U.S. Application Data

(63) Continuation of application No. 17/172,387, filed on Feb. 10, 2021, which is a continuation-in-part of (Continued)

(51) Int. Cl.
*A61K 38/08* (2019.01)
*A61K 9/00* (2006.01)
(Continued)

(52) U.S. Cl.
CPC .......... *A61K 38/08* (2013.01); *A61K 9/0053* (2013.01); *A61K 39/3955* (2013.01);
(Continued)

(58) Field of Classification Search
None
See application file for complete search history.

(56) References Cited

U.S. PATENT DOCUMENTS 8,034,776 B2   10/2011   Fasano et al.
8,168,594 B2    5/2012   Paterson et al.
(Continued)

FOREIGN PATENT DOCUMENTS

WO   2012/145632   10/2012
WO   2017/173321   10/2017
(Continued)

OTHER PUBLICATIONS

Acharya et al., Tim-3 finds its place in the cancer immunotherapy landscape, J. Immunother. Canc. 8: e000911, pp. 1-11, 2020.*
(Continued)

*Primary Examiner* — Claire Kaufman
(74) *Attorney, Agent, or Firm* — Morgan, Lewis & Bockius LLP

(57) ABSTRACT

The present invention provides compositions and methods for treating a patient having cancer, as well as methods for potentiating an immune checkpoint inhibitor therapy. The methods comprise administering larazotide or a derivative thereof such as (d)-larazotide to a subject in need, including subjects undergoing checkpoint inhibitor therapy, and subjects scheduled to undergo immune checkpoint inhibitor therapy.

23 Claims, 20 Drawing Sheets

Specification includes a Sequence Listing.

Related U.S. Application Data application No. 16/982,115, filed as application No. PCT/US2019/022885 on Mar. 19, 2019.

(60) Provisional application No. 62/644,723, filed on Mar. 19, 2018.

(51) Int. Cl.
*A61P 35/00* (2006.01)
*A61K 39/395* (2006.01)
*A61K 39/00* (2006.01)

(52) U.S. Cl.
CPC ........ *A61P 35/00* (2018.01); *A61K 2039/505* (2013.01); *A61K 2039/545* (2013.01)

(56) References Cited

U.S. PATENT DOCUMENTS

| | | | |
|---|---|---|---|
| 8,299,017 | B2 | 10/2012 | Paterson et al. |
| 8,709,416 | B2 | 4/2014 | Langermann et al. |
| 8,785,374 | B2 | 7/2014 | Tamiz |
| 8,796,203 | B2 | 8/2014 | Paterson et al. |
| 8,957,032 | B2 | 2/2015 | Alkan et al. |
| 9,241,969 | B2 | 1/2016 | Paterson et al. |
| 9,265,811 | B2 | 2/2016 | Paterson et al. |
| 9,279,807 | B2 | 3/2016 | Fasano et al. |
| 10,526,372 | B2 | 1/2020 | Alkan et al. |
| 10,723,763 | B2 | 7/2020 | Paterson et al. |
| 2015/0164978 | A1 | 6/2015 | Paterson et al. |
| 2016/0022760 | A1 | 1/2016 | Perrow et al. |
| 2018/0271932 | A1 | 9/2018 | Perrow et al. |
| 2019/0358288 | A1 | 11/2019 | Madan et al. |
| 2019/0358289 | A1 | 11/2019 | Madan et al. |
| 2020/0231626 | A1 | 7/2020 | Alkan et al. |
| 2020/0392186 | A1 | 12/2020 | Madan et al. |
| 2021/0030814 | A1 | 2/2021 | Madan |
| 2021/0069286 | A1 | 3/2021 | Prior et al. |
| 2021/0100868 | A1 | 4/2021 | Blikslager |

FOREIGN PATENT DOCUMENTS

| | | |
|---|---|---|
| WO | 2018/187272 | 10/2018 |
| WO | 2020227341 | 11/2020 |
| WO | 2021/034629 | 2/2021 |

OTHER PUBLICATIONS

Ju et al., Drug delivery vectors based on filamentous bacteriophages and phage-mimetic nanoparticles, Drug. Deliv. 24:1, 1898-1908, Dec. 2017.*

Leech et al., Paradigms lost—an emerging role for over-expression of tight junction adhesion proteins in cancer pathogenesis, Ann. Trend Med. 3(13):184, 2015.*

Slifer et al.Larazotide acetate: a pharmacological peptide approach to tight junction regulation Am. J. Physiol. Gastrointest. Liver Physiol. 320:G983-G989, 2021.*

Martin et al., Loss of tight junction barrier function and its role in cancer metastasis, Biochim. Biophys. Acta, 1788:872-891, 2009.*

Van den Eynde et al., Is there a clinical future for IDO1 inhibitors after the failure of epacadostatin melanoma? Ann. Rev. Canc. Biol., 4:241-256, 2020.*

Pearce, SC et al., Marked differences in tight junction composition and macromolecular permeability among different intestinal cell types, BMC Biology. Feb. 1, 2018, vol. 16, No. 1; 18 pp. 1-16.

International Search Report and Written Opinion for International Application No. PCT/US2019/022885, dated May 24, 2019, 11 pages.

* cited by examiner

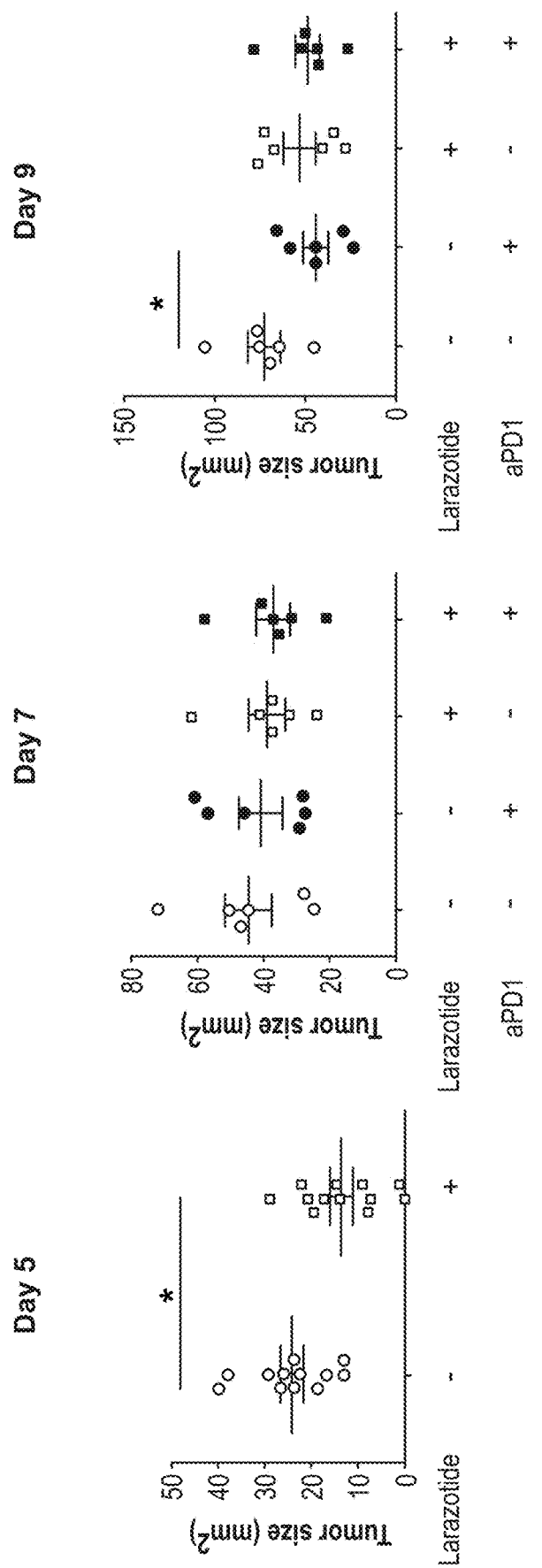

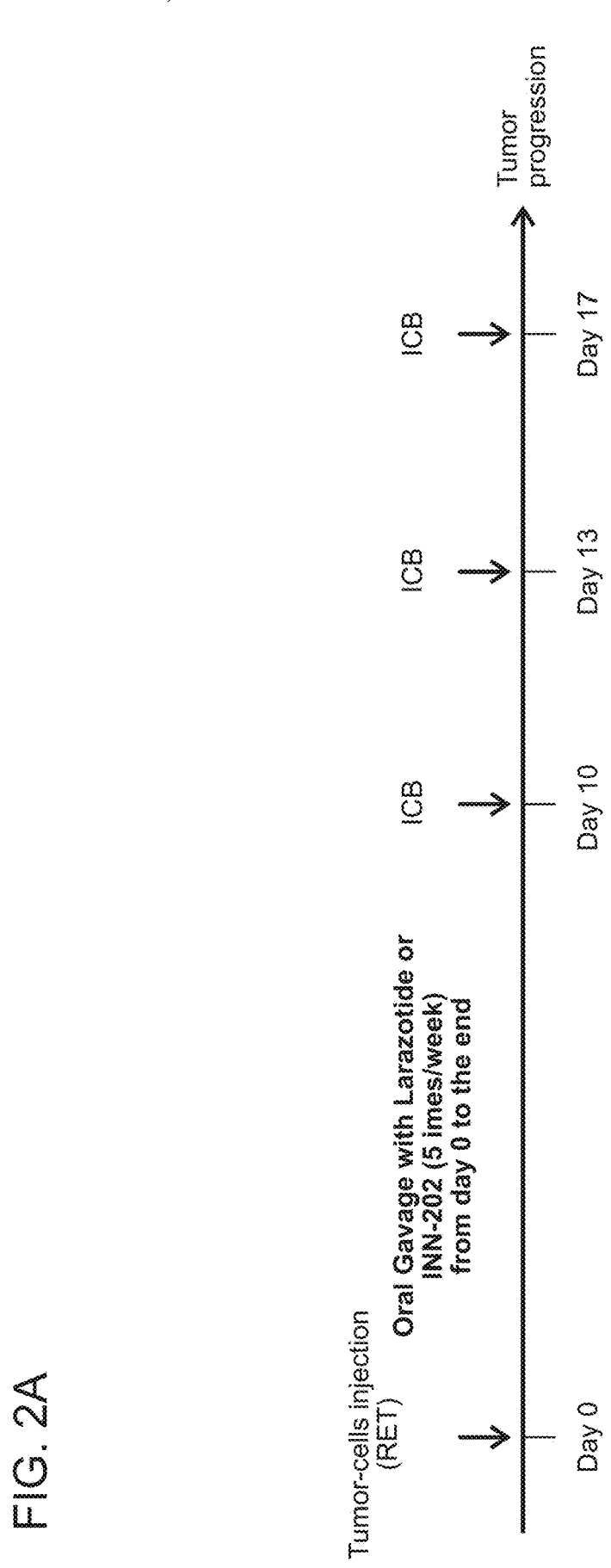

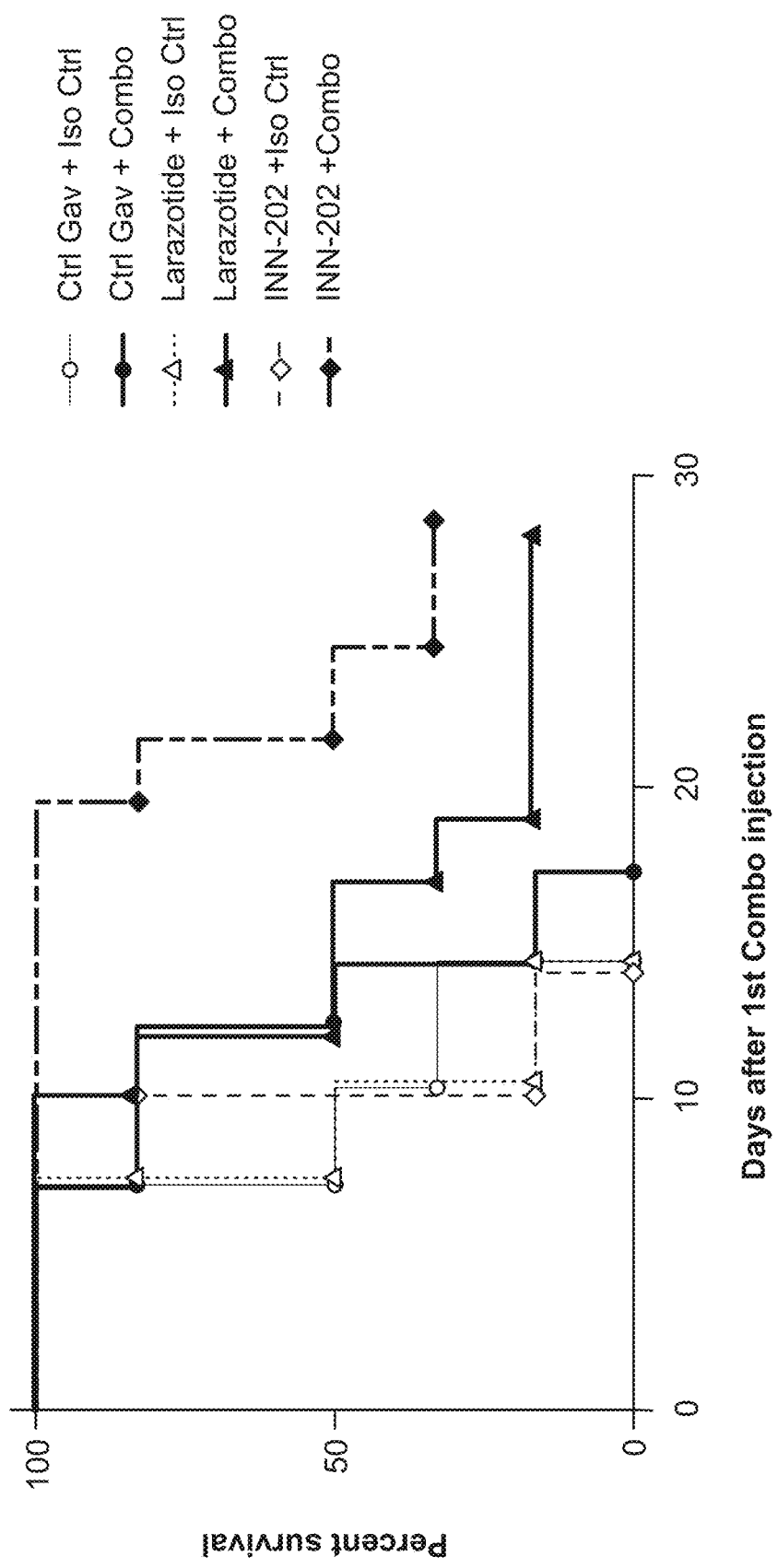

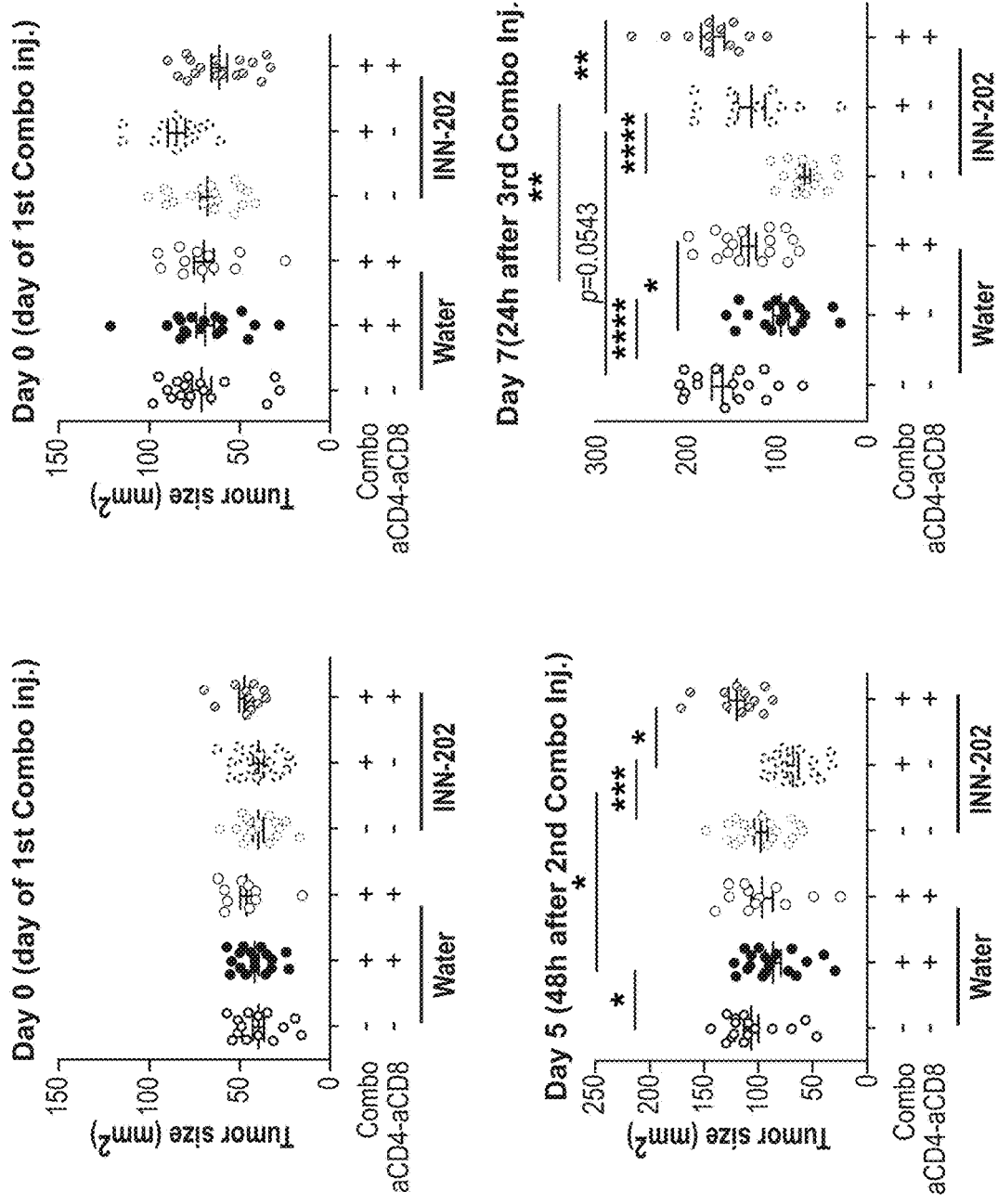

TREATMENT OF CANCER WITH LARAZOTIDE DERIVATIVES IN COMBINATION WITH IMMUNE CHECKPOINT INHIBITORS

CROSS-REFERENCE TO RELATED APPLICATIONS

This application is a continuation application of U.S. application Ser. No. 17/172,387, filed Feb. 10, 2021, which is a continuation in part of U.S. application Ser. No. 16/982,115, filed Sep. 18, 2020, which is a 371 National Stage Entry of International Application No. PCT/US2019/022885, filed Mar. 19, 2019, which claims the benefit of U.S. Provisional Application No. 62/644,723 filed on Mar. 19, 2018, the entire contents of which are incorporated herein.

DESCRIPTION OF THE TEXT FILE SUBMITTED ELECTRONICALLY

The contents of the text file submitted electronically herewith are incorporated herein by reference in their entirety: A computer readable format copy of the Sequence Listing (Filename: "NMT-017CPC1_ST25.txt"; Date created: Apr. 13, 2021; File size: 1,881 bytes).

BACKGROUND

Immune checkpoint inhibitors have emerged as important therapeutic options for a variety of cancers, including PD-1 blockade therapy. However, many patients fail to respond, or fully respond, to the therapy. For example, some patients have shown no response to anti-PD-1 treatment. In some instances, patients demonstrate an encouraging initial response only to acquire resistance to the therapy.

Accordingly, there is a need for methods to improve the efficacy of treatment with immune checkpoint inhibitors.

SUMMARY

The present invention provides compositions and methods for treating a patient having cancer, as well as methods for potentiating an immune checkpoint inhibitor therapy. The methods comprise administering larazotide or a derivative thereof to a subject in need, including subjects undergoing checkpoint inhibitor therapy, and subjects scheduled to undergo immune checkpoint inhibitor therapy. In exemplary embodiments, (d)-larazotide is administered.

Larazotide is a peptide that promotes tight junction integrity and reduces paracellullar permeability, including permeability of the intestinal epithelium. In accordance with this disclosure, larazotide administration, or administration of a larazotide derivative (e.g., having one or more (d)-amino acids, potentiates immune checkpoint inhibitor therapy. Exemplary immune checkpoint inhibitors that can be potentiated with larazotide treatment include those selected from an inhibitor of: Programmed Death-Ligand 1 (PD-L1), Programmed Death 1 (PD-1), CTLA-4, and PD-L2, among others, as well as combinations of immune checkpoint inhibitor agents.

In some embodiments, larazotide or derivative is administered to potentiate the efficacy of the immune checkpoint inhibitor therapy, including for subjects that showed no response or only a partial response to prior treatment with an immune checkpoint inhibitor therapy. In some embodiments, the patient did not achieve at least stable disease through prior treatment with an immune checkpoint inhibitor therapy. In some embodiments, the prior immune checkpoint inhibitor therapy was a PD-1 blockade therapy (e.g., anti-PD-1 or anti-PD-L1). In some embodiments, (d)-larazotide is administered.

In some embodiments, the larazotide or a derivative is administered to the gastrointestinal tract or parenterally. Larazotide and its derivatives are effective for improving integrity of tight junctions of epithelial cells (including epithelial cells if the gastrointestinal mucosa), as well endothelial cells.

In some embodiments, the pharmaceutical composition comprising larazotide or derivative is formulated for targeted delivery to the gastrointestinal tract including the small intestine and/or large intestine. In some embodiments, the pharmaceutical composition is formulated to release larazotide or a derivative thereof in the small intestine, for example, in one or more of the duodenum, jejunum, and the ileum. In some embodiments, the pharmaceutical composition is formulated to release (or to also release) larazotide or a derivative thereof in the large intestine, for example, in one or more of the cecum, the ascending colon, the transverse colon, the descending colon, and the sigmoid colon.

In some embodiments, the pharmaceutical composition is formulated to have sustained-release profiles, i.e., slow release of the larazotide or a derivative thereof in the GI tract over an extended period of time. For example, the formulation may deliver and/or functionally release from 0.5 to about 5 mg of larazotide or derivative over the course of at least about 2 hours. Sustained release formulations will allow the composition to be applied at larger portions of the GI tract, while avoiding loss of efficacy from an inverse dose response observed with larazotide. In some embodiments, the formulation releases larazotide (or derivative) in a form that provides for a local sustained release at one or more locations, including sustained release from particles, gels, emulsions, or biodegradable matrix. For example, the sustained or controlled release composition begins to release peptide starting within about 5 to 30 minutes of exposure to simulated intestinal fluid, with release of peptide continuing for at least about 180 minutes of exposure to simulated intestinal fluid. Release profiles can be prepared, for example, using particles with different enteric polymer coats and/or different thicknesses of the polymer coats.

In some embodiments, compositions comprising or releasing larazotide or a derivative thereof are administered at least once per day (e.g., from 1 to 5 times daily). In some embodiments, the larazotide regimen is initiated before checkpoint inhibitor therapy, for example, at least one week prior to initiation of checkpoint inhibitor therapy to prepare the patient for the immune checkpoint inhibitor therapy. In these or other embodiments, the regimen is continued throughout the duration of checkpoint inhibitor therapy, and optionally for a period of time thereafter.

The cancer can be any cancer treatable by immune checkpoint inhibitor therapy, including primary cancers and metastatic cancers.

Other aspects and embodiments will be apparent from the following detailed description.

BRIEF DESCRIPTION OF THE DRAWINGS

FIG. 1A shows the experimental protocol. FIG. 1B shows tumor size with or without larazotide treatment, anti-PD1 antibody, or both through Day 19. FIG. 1C depicts tumor growth kinetics for mice in each group. The experiment is conducted with n=6 mice per group. Mann Whitney test or ANOVA statistical analyses: *p<0.05, p<0.01, *p<0.001. FIG. 1D shows that intestinal permeability is barely disrupted by tumor inoculation with no effect of larazotide treatment. Data depict the mean and the experiment is conducted with at least n=5 mice per group. Mann Whitney test or ANOVA statistical analyses: *p<0.05, p<0.01, *p<0.001.

FIG. 2A-D show that (d)-larazotide (INN-202) improves the efficacy of ICB (anti-CTLA4+anti-PD1 antibodies) against RET orthotopic melanoma. FIG. 2A depicts use of a RET-melanoma model and the administration of a combination of anti-PD1 and anti-CTLA4 antibodies via intraperitoneal administration along with oral larazotide or (d)-larazotide. The effects of larazotide or (d)-larazotide oral gavage on cross-sectional tumor sizes are shown in FIG. 2B, and the effects on longitudinal tumor growth kinetics of RET-melanoma are depicted as means+/−SEM of tumor sizes at different time points for 6 animals/group are shown in FIG. 2C. FIG. 2D shows the corresponding curves indicating overall survival. Mann Whitney test or ANOVA statistical analyses: *p<0.05, p<0.01, *p<0.001.

FIGS. 3A-C depicts ELISA monitoring of Lipocalin-2 in the feces of mice injected with RET-melanoma cells without ICB (FIG. 3A), or plasma sST2 (FIG. 3B) and plasma sCD14 (FIG. 3C) in mice treated or not treated with larazotide or (d) larazotide (INN-202) and water.

FIG. 4A shows the experimental protocol performed three times. FIG. 4B shows the effect of (d)-larazotide oral gavage on cross-sectional tumor sizes, and FIG. 4C shows the effect on longitudinal tumor growth kinetics of RET-melanoma, depicted as means+/−SEM of tumor sizes at different time points for 18 animals gathered from 3 independent experiments. Mann Whitney test or ANOVA statistical analyses: *p<0.05, p<0.01, *p<0.001.

FIG. 5A-C depict the combination of (d)-larazotide (INN-202) and ICB mediating T cell-dependent anti-melanoma effects. FIG. 5B-C show cross-sectional tumor sizes (FIG. 5B) and longitudinal tumor growth kinetics (FIG. 5C) of RET-melanoma of anti-CD4 and anti-CD8 depleting antibodies on the combination of (d)-larazotide oral gavage and ICB against RET melanoma. Mann Whitney test or ANOVA statistical analyses: *p<0.05, p<0.01, *p<0.001.

DETAILED DESCRIPTION

Figure 1A:
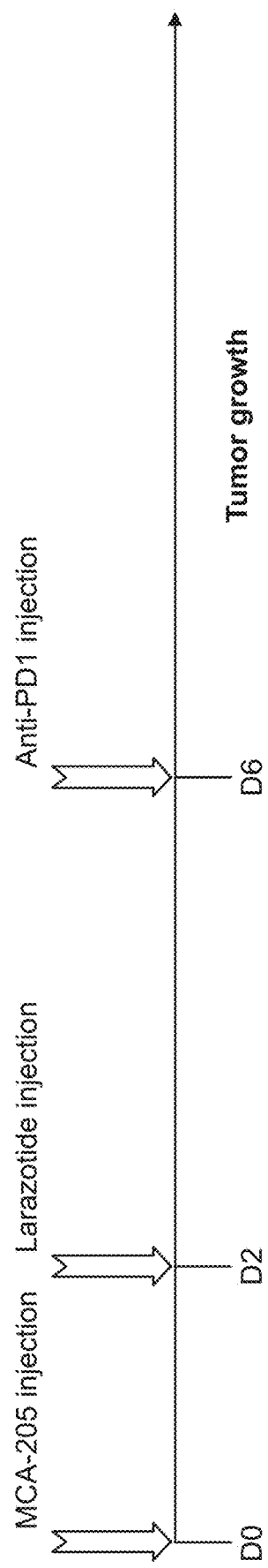
FIG. 1A-D depict larazotide transiently reducing the spontaneous growth of MCA205 sarcoma by measuring the tumor growth curve of MCA205 sarcoma in C57BL/6 mice in the presence of systemic administration of ICB and larazotide.

The present invention provides compositions and methods for potentiating an immune checkpoint inhibitor therapy, including for the treatment of cancer. The methods comprise administering larazotide or a derivative thereof to a subject in need, including subjects undergoing checkpoint inhibitor therapy, and subjects scheduled to undergo immune checkpoint inhibitor therapy.

The barrier properties of the intestinal epithelium are regulated by specialized plasma membrane structures known as tight junctions. Alterations in tight junctions can result in disruptions of the intestinal barrier functions and increased intestinal permeability. An intact intestinal barrier prevents the permeation of pathogens, antigens, endotoxins, and other proinflammatory substances into the body. Alterations in tight junctions, e.g. leaky tight junctions, can disrupt the homeostasis of the gut microbiome. It is believed that the maintenance of a healthy gut mucosa can lead to the improved efficacy of checkpoint inhibitor therapy. Larazotide is a peptide that promotes tight junction integrity and reduces paracellullar permeability, including permeability of the intestinal epithelium, and is a candidate to potentiate immune checkpoint inhibitor therapy.

Larazotide has the amino acid sequence: Gly Gly Val Leu Val Gln Pro Gly (SEQ ID NO: 1). Derivatives of larazotide comprise from one to five amino acid modifications with respect to SEQ ID NO: 1, and the modifications may be independently selected from substitutions, deletions, insertions or additions with respect to SEQ ID NO: 1. In some embodiments, the larazotide derivative is a derivative having 1, 2, 3, 4, or 5 amino acid deletions, insertions, and/or substitutions with respect to SEQ ID NO: 1. By way example, in some embodiments, the larazotide derivative is a derivative described in U.S. Pat. Nos. 8,785,374, 8,957,032, and 9,279,807, which are hereby incorporated by reference in their entirety. In some embodiments, the derivative has one or more non-genetically encoded amino acids, or one or more (or all) (d)-amino acids. The term "larazotide" or "larazotide treatment" refers to treatment with larazotide or a derivative that promotes tight junction integrity.

Exemplary derivatives of larazotide include:

```
                                            (SEQ ID NO: 2)
        Gly Arg Val Cys Val Gln Pro Gly;

(SEQ ID NO: 3)
        Gly Arg Val Cys Val Gln Asp Gly;

(SEQ ID NO: 4)
        Gly Arg Val Leu Val Gln Pro Gly;

(SEQ ID NO: 5)
        Gly Arg Val Leu Val Gln Asp Gly;

(SEQ ID NO: 6)
        Gly Arg Leu Cys Val Gln Pro Gly;

(SEQ ID NO: 7)
        Gly Arg Leu Cys Val Gln Asp Gly;

(SEQ ID NO: 8)
        Gly Arg Leu Leu Val Gln Pro Gly;

(SEQ ID NO: 9)
        Gly Arg Leu Leu Val Gln Asp Gly;

(SEQ ID NO: 10)
        Gly Arg Gly Cys Val Gln Pro Gly;

(SEQ ID NO: 11)
        Gly Arg Gly Cys Val Gln Asp Gly;

(SEQ ID NO: 12)
        Gly Arg Gly Leu Val Gln Pro Gly;

(SEQ ID NO: 13)
        Gly Arg Gly Leu Val Gln Asp Gly;

(SEQ ID NO: 14)
        Gly Gly Val Cys Val Gln Pro Gly;

(SEQ ID NO: 15)
        Gly Gly Val Cys Val Gln Asp Gly;

(SEQ ID NO: 16)
        Gly Gly Val Leu Val Gln Asp Gly;
```

```
                                    (SEQ ID NO: 17)
Gly Gly Leu Cys Val Gln Pro Gly;

(SEQ ID NO: 18)
Gly Gly Leu Cys Val Gln Asp Gly;

(SEQ ID NO: 19)
Gly Gly Leu Leu Val Gln Pro Gly;

(SEQ ID NO: 20)
Gly Gly Leu Leu Val Gln Asp Gly;

(SEQ ID NO: 21)
Gly Gly Gly Cys Val Gln Pro Gly;

(SEQ ID NO: 22)
Gly Gly Gly Cys Val Gln Asp Gly;

(SEQ ID NO: 23)
Gly Gly Gly Leu Val Gln Pro Gly;
and (SEQ ID NO: 24)
Gly Gly Gly Leu Val Gln Asp Gly.
```

In some embodiments, the treatment is with (d)-larazotide, that is, where all non-glycine residues are in the (d) form.

In some embodiments, the one or more immune checkpoint inhibitors are selected from an inhibitor of: Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CDI37, CDI60, CD226, CD276, DR3, GALS, GITR, HAVCR2, HVEM, IDOL ID02, ICOS (inducible T cell costimulator), KIR, LAIRI, LIGHT, MARCO (macrophage receptor with collagenous structure), PS (phosphatidylserine), OX-40, SLAM, TIGHT, VISTA, and VTCNI. In some embodiments, the immune checkpoint inhibitor is an inhibitor of PD-1 or PD-L1 (i.e., a PD-1 blockade therapy). In some embodiments, the immune checkpoint inhibitor is selected from ipilimumab, tremelimumab, pembrolizumab and nivolumab.

In some embodiments, the subject showed no response or only a partial response to prior treatment with an immune checkpoint inhibitor therapy. In some embodiments, the patient did not achieve at least stable disease through prior treatment with an immune checkpoint inhibitor therapy. In some embodiments, the prior immune checkpoint inhibitor therapy was a PD-1 blockade therapy (e.g., anti-PD-1 or anti-PD-L1).

In some embodiments, the immune checkpoint inhibitor is a monoclonal antibody, such as anti-CTLA-4, anti-PD-1, or anti-PD-L1 and/or PD-L2 agent (e.g. YERVOY, OPDIVO, or KEYTRUDA, or comparable agents thereto). In various embodiments, these agents can be administered in a plurality of doses, such as from 4 to 12 doses or from 4 to 8 doses, which can be administered over a 1-4 month period of time in some embodiments (e.g., 1 or 2 months in some embodiments). In some embodiments, the subject receives combination therapy with an anti-CTLA-4 antibody and a PD-1 blockade therapy, along with larazotide or derivative (e.g., (d)-larazotide).

In some embodiments, the subject further receives a probiotic. Probiotics suitable for use in the present invention include, but are not limited to, *Saccharomyces boulardii*; *Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+ CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve*, and *Streptococcus salivarius* subsp. *thermophilus* (VSL #3)).

In accordance with embodiments of the invention, larazotide or a derivative thereof may be delivered in a larazotide-producing probiotic strain heterologously expressed in a microorganism that is a commensal microorganism of the human gastrointestinal tract, or a microbial species that find conventional use as a probiotic, as described in International Application No. PCT/US19/19348, which is hereby incorporated by reference in its entirety. For example, the microorganism may be a bacterium or fungus, and exemplary microorganisms include those of the genus *Saccharomyces, Lactobacillus, Clostridium, Streptococcus, Staphylococcus*, or *Bifidobacterium*. For example, the microorganism may be a species selected from *Saccharomyces boulardii, Lactobacillus rhamnosus, Lactobacillus plantarum, Clostridium butyricum*, non-toxigenic *Clostridium difficile, Lactobacillus casei, Lactobacillus acidophilus, Lactobacillus bulgaricus, Streptococcus thermophilus, Bifidobacterium bifidum, Bifidobacterium longum, Bifidobacterium lactis, Bifidobacterium infantis, Bifidobacterium breve*, and *Streptococcus salivarius*. In some embodiments, a probiotic strain (bacterial or fungal) is engineered for expression and optionally secretion of larazotide or derivative thereof from the cell.

In various embodiments, the microorganism is derived from a commensal microorganism of the human gastrointestinal tract, such as those of the genera *Bacteroides, Faecalibacterium, Corynebacterium, Eubacterium, Ruminococcus, Peptococcus, Peptostreptococcus, Escherichia*, or *Helicobacter*. In some embodiments, the microbe is *E. coli*.

In some embodiments, the microbe is selected from a Fungal genera of *Candida, Saccharomyces, Aspergillus, Penicillium, Rhodotorula, Trametes, Pleospora, Sclerotinia, Bullera*, and *Galactomyces*.

Where larazotide or derivative is delivered as a larazotide-producing probiotic, the probiotic may be delivered, for example, about once daily, about once weekly, or about once monthly.

In accordance with embodiments of the invention, larazotide or a derivative thereof may be delivered in a larazotide-encoding bacteriophage that infects microbes in the GI tract of the subject. In some embodiments, the present invention contemplates a bacteriophage comprising a polynucleotide encoding a peptide that comprises the amino acid sequence of larazotide (SEQ ID NO: 1) or a derivative thereof. The polynucleotide further comprises a promoter controlling expression of the polynucleotide in a host bacterium, as described. The host bacterium may be of the genus *Lactobacillus, Clostridium, Streptococcus*, or *Bifidobacterium*.

Generally, the host bacterium is a commensal microorganism of the human gastrointestinal tract, and may belong to the genera *Bacteroides, Faecalibacterium, Eubacterium, Ruminococcus, Peptococcus, Peptostreptococcus, Escherichia*, or *Helicobacter*. In some embodiments, the host bacterium is *E. coli*.

The bacteriophage may further encode a secretory signal at the N-terminus of the peptide (as described), so as to drive secretion of the peptide from the host cell. The secretory signal may be cleaved by the host bacteria upon export of the peptide out of the cell. Various types of bacteriophages may be engineered in accordance with these embodiments, including lytic and lysogenic bacteriophages. In some embodiments, the phage is a lytic phage, allowing release of peptide upon lysis of the host cell, rather than through use of a signal peptide.

Exemplary bacteriophages include those of the order Caudovirales, Siphoviridae, Myoviridae, or Podoviridae.

In some embodiments, the bacteriophage is a coliphage, such as lambda phage, M13, T7, T4, or T3 bacteriophage. In other embodiments, the bacteriophage is *lactobacillus* phage, such as phages infecting *Lactobacillus delbrueckii* subsp. *bulgaricus*, known as Ld3, Ld17, and Ld25A. Casey E., *Molecular Characterization of Three Lactobacillus delbrueckii subsp. bulgaricus Phages, Appl. Environ. Microbiol.* 2014 vol. 80 no. 18 5623-5635. Phages can be engineered to optimize the spectrum of infection. Various other phages have been isolated from human feces, which can be used in accordance with this disclosure. Breitbart M, *Metagenomic Analyses of an Uncultured Viral Community from Human Feces, J Bacteriol. Vol.* 185, No. 20 pages 6220-6223 (2003).

In some embodiments, the larazotide or a derivative thereof (e.g., (d)-larazotide) is administered to the gastrointestinal tract or parenterally (e.g., by intravenous infusion). Larazotide and its derivatives are effective for improving integrity of tight junctions of epithelial cells (including epithelial cells if the gastrointestinal mucosa), as well endothelial cells.

In some embodiments, the larazotide is administered in any suitable form, including as a salt. By way of example, in some embodiments, the larazotide is administered as an acetate salt or a hydrochloride salt. Non-limiting examples of salts of larazotide are disclosed in US 2013/0281384, which is hereby incorporated by reference in its entirety. Alternative salts may be employed, including any pharmaceutically acceptable salt of the peptide, for example, such as those listed in Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety.

In some embodiments, the larazotide or derivative thereof is administered as a pharmaceutical composition. Pharmaceutical compositions can take the form of tablets, pills, pellets, capsules, capsules containing liquids, capsules containing multiparticulates, powders, solutions, emulsion, drops, suppositories, suspensions, delayed-release formulations, sustained-release formulations, controlled-release formulations, or any other form suitable for use. The pharmaceutical compositions are formulated for oral administration (administration to the GI). In some embodiments, the composition is formulated for intravenous infusion.

In some embodiments, the pharmaceutical composition comprising larazotide (or derivative such as (d)-larazotide) is formulated for targeted delivery to the gastrointestinal tract including the stomach, small intestine, and large intestine including a plurality of subsections thereof. In some embodiments, the pharmaceutical composition is formulated to release larazotide or a derivative thereof in the small intestine, for example, in one or more of the duodenum, jejunum, and the ileum. In some embodiments, the pharmaceutical composition is formulated to release larazotide or a derivative thereof in the large intestine, for example, in one or more of the cecum, the ascending colon, the transverse colon, the descending colon, and the sigmoid colon.

In some embodiments, the pharmaceutical composition is formulated so as to not substantially release or partially release larazotide or a derivative thereof in the stomach, but to release the peptide agent after entry into the small bowel. In some embodiments, the pharmaceutical composition is formulated to have a delayed-release profile, i.e., not immediately release the peptide agent upon ingestion; but rather, postponement of release until the pharmaceutical composition is lower in the gastrointestinal tract. By way of example, in some embodiments, the pharmaceutical composition is formulated for release of the peptide agent in the small intestine (e.g., one or more of duodenum, jejunum, and ileum) and/or the large intestine (e.g., one or more of cecum, ascending, transverse, descending and/or sigmoid portions of the colon). In some embodiments, the pharmaceutical composition is formulated to have a delayed-release profile as described in, for example, U.S. Pat. No. 8,168,594, the entire contents of which are hereby incorporated by reference.

In some embodiments, the pharmaceutical composition remains essentially intact, or may be essentially insoluble, in gastric fluid. In some embodiments, the stability of the delayed-release coating is pH dependent. Without being bound by theory, in some embodiments, delayed-release coatings that are pH dependent are substantially stable in acidic environments (pH of about 5 or less), and substantially unstable in near neutral to alkaline environments (pH greater than about 5). For example, in some embodiments, the delayed-release coating essentially disintegrates or dissolves in near neutral to alkaline environments such as are found in the small intestine (e.g., one or more of the duodenum, jejunum, and ileum) and/or large intestine (e.g., one or more of the cecum, ascending colon, transverse colon, descending colon, and sigmoid colon).

In some embodiments, the pharmaceutical composition is formulated to have sustained-release profiles, i.e., slow release of the larazotide or a derivative thereof (e.g., (d)-larazotide) in the GI tract over an extended period of time. In various embodiments, the larazotide or derivative is administered in a sustained release or controlled release formulation. For example, the formulation may deliver and/or functionally release from 0.5 to about 5 mg of larazotide or derivative, or from about 0.5 to about 4 mg of larazotide or derivative, or from about 0.5 to about 3 mg of larazotide or derivative, or from about 0.5 to about 2 mg of larazotide or derivative, or from about 0.5 to about 1 mg of larazotide or derivative. In various embodiments, the sustained release or controlled release formulation contains at least 1 mg or at least 2 mg of larazotide or derivative. For example, the formulation may contain from about 1 mg to about 5 mg of larazotide or derivative, or about 1 mg to about 3 mg of larazotide or derivative.

The sustained or controlled release formulation may functionally release peptide over the course of at least about 2 hours, or at least about 2.5 hours, or at least about 3 hours, or at least about 4 hours, or at least about 5 hours. The term "functional release" refers to the release of larazotide or derivative such that the larazotide peptide can interact with cells of the intestinal epithelium to promote tight junction assembly. In various embodiments, larazotide or derivative is formulated as a plurality of particles that release larazotide or derivative at different times in intestinal fluid, or at different locations in the intestine. In other embodiments, the formulation releases larazotide or derivative in a form that provides for a local sustained release at one or more locations, including sustained release from particles, gels, emulsions, or biodegradable matrix. In some embodiments, the sustained or controlled release composition (e.g., comprising peptide-containing particles, gels, emulsions, or biodegradable matrix) begins to release peptide starting within about 5 to 30 minutes of exposure to simulated intestinal fluid, with release of peptide continuing for at least about 180 minutes, or at least about 210 minutes, or at least about 240 minutes, or at least about 280 minutes of exposure to simulated intestinal fluid. For example, after about 3 hours, at least 90% of the peptide agent has been released. Release profiles can be prepared, for example, using particles with different enteric polymer coats and/or different thicknesses of the polymer coats. Exemplary particles are described herein.

By way of example, in some embodiments, the larazotide, and/or a derivative thereof is administered to the small intestine of the patient, as an oral dosage, delayed-release composition that contains larazotide (or a derivative thereof)-coated beads that are stable in gastric fluid and unstable in intestinal fluid so as to substantially release the peptide in the small intestine. In an exemplary oral dosage composition, an effective amount of larazotide (e.g., as the acetate salt) is provided in first delayed-release particles that are capable of releasing larazotide or derivative in the duodenum of a patient, and second delayed release particles that are capable of releasing larazotide or derivative in the jejunum of a patient, and optionally a third delayed release particle capable of releasing larazotide or derivative in the ileum of a patient. Each particle may have a core particle, a coat comprising larazotide or derivative over the core particle, and a delayed-release coating (e.g., a 1:1 co-polymer of acrylate and methacrylate) outside the coat comprising larazotide or derivative. The first delayed-release particles may release at least 70% of the larazotide or derivative in the first delayed-release particles by about 60 minutes of exposure to simulated intestinal fluid having a pH of greater than 5; the second delayed-release particles may release at least 70% of the larazotide or derivative by about 30 and about 90 minutes of exposure to simulated intestinal fluid having a pH of greater than 5. The third delayed-release particles may release at least 70% of the larazotide or derivative by about 120 minutes to about 240 minutes (e.g., about 120 minutes to about 180 minutes) of exposure to simulated intestinal fluid.

In some embodiments, the larazotide, or derivative thereof, is administered to the colon of a patient, which can be via the same or different composition for administration to the small intestine. Various colon-specific delivery approaches may be utilized. For example, in some embodiments, the modified release formulation is formulated using a colon-specific drug delivery system (CODES), as described for example, in Li et al., AAPS PharmSciTech (2002), 3(4): 1-9, the entire contents of which are incorporated herein by reference. Drug release in such a system is triggered by colonic microflora coupled with pH-sensitive polymer coatings.

In some embodiments, the formulation is designed as a core tablet with three layers of polymer. The first coating is an acid-soluble polymer (e.g., EUDRAGIT E), the outer coating is enteric, along with a hydroxypropyl methylcellulose barrier layer interposed in between. In some embodiments, colon delivery is achieved by formulating the larazotide or derivative with specific polymers that degrade in the colon such as, for example, pectin. The pectin may be further gelled or cross-linked with a cation such as a zinc cation. Additional colon specific formulations include, but are not limited to, pressure-controlled drug delivery systems (prepared with, for example, ethylcellulose) and osmotic controlled drug delivery systems (i.e., ORDS-CT).

In some embodiments, the delayed-release coating includes an enteric agent that is substantially stable in acidic environments and substantially unstable in near neutral to alkaline environments. In some embodiments, the delayed-release coating contains an enteric agent that is substantially stable in gastric fluid. By way of example, in some embodiments, the enteric agent is selected from: solutions or dispersions of methacrylic acid copolymers, cellulose acetate phthalate, hydroxypropylmethyl cellulose phthalate, polyvinyl acetate phthalate, carboxymethylethylcellulose, EUDRAGIT®-type polymer (poly(methacrylic acid, methylmethacrylate), hydroxypropyl methylcellulose acetate succinate, cellulose acetate trimellitate, shellac, or other suitable enteric coating polymers. In some embodiments, the EUDRAGIT®-type polymer is selected from, for example, EUDRAGIT® FS 30D, L 30 D-55, L 100-55, L 100, L 12.5, L 12.5 P, RL 30 D, RL PO, RL 100, RL 12.5, RS 30 D, RS PO, RS 100, RS 12.5, NE 30 D, NE 40 D, NM 30 D, S 100, S 12.5, and S 12.5 P. In some embodiments, one or more of EUDRAGIT® FS 30D, L 30 D-55, L 100-55, L 100, L 12.5, L 12.5 P RL 30 D, RL PO, RL 100, RL 12.5, RS 30 D, RS PO, RS 100, RS 12.5, NE 30 D, NE 40 D, NM 30 D, S 100, S 12.5 and S 12.5 P is used. In some embodiments, the enteric agent is a combination of any of the foregoing solutions or dispersions.

In some embodiments, the delayed-release coating degrades as a function of time when in aqueous solution without regard to the pH and/or presence of enzymes in the solution. In some embodiments, such a delayed-release coating comprises a water insoluble polymer. In some embodiments, the delayed-release coating's solubility in aqueous solution is independent of the pH. The term "pH independent" as used herein means that the water permeability of the polymer and its ability to release pharmaceutical ingredients is not a function of pH and/or is only very slightly dependent on pH. In some embodiments, such a delayed-release coating is used to prepare, for example, sustained release formulations. In some embodiments, suitable water insoluble polymers include, for example, pharmaceutically acceptable non-toxic polymers that are substantially insoluble in aqueous media, e.g., water, independent of the pH of the solution. In some embodiments, suitable water insoluble polymers include, for example, cellulose ethers, cellulose esters, and cellulose ether-esters, i.e., a cellulose derivative in which some of the hydroxy groups on the cellulose skeleton are substituted with alkyl groups and some are modified with alkanoyl groups. In some embodiments, suitable water insoluble polymers include, for example, ethyl cellulose, acetyl cellulose, nitrocellulose, and the like. In some embodiments, suitable water insoluble polymers include, for example, lacquer, and acrylic and/or methacrylic ester polymers, polymers or copolymers of acrylate or methacrylate having a low quaternary ammonium content, or mixture thereof and the like. In some embodiments, suitable water insoluble polymers include, for example, EUDRAGIT RS®, EUDRAGIT RL®, EUDRAGIT NE®, polyvinyl esters, polyvinyl acetals, polyacrylic acid esters, butadiene styrene copolymers, and the like. In some embodiments, the delayed-release coating comprises a combination of any of the foregoing water insoluble polymers.

In some embodiments, the pharmaceutical composition releases multiple doses of the larazotide, or a derivative thereof along the gastrointestinal tract. For example, in some embodiments, the pharmaceutical composition and/or formulation releases multiple doses of the larazotide or a derivative thereof at different locations along the intestines, at different times, and/or at different pH. In some embodiments, the overall release profile of such a formulation is adjusted using, for example, multiple particle types or multiple layers. For example, in some embodiments, the first dose of the larazotide, and/or a derivative thereof (or salt thereof), is formulated for release in, for example, the small intestine (e.g., one or more of duodenum, jejunum, ileum), whereas the second dose is formulated for delayed release in, for example, the large intestines (e.g., one or more of cecum, ascending, transverse, descending or sigmoid portions of the colon, and rectum). In another example, the first dose of the larazotide, and/or a derivative thereof is formulated for release in, for example, the small intestine (e.g., one or more of duodenum, jejunum, ileum), whereas the second dose is formulated for delayed release in, for example, another part of the small intestine (e.g., one or more of duodenum, jejunum, ileum). In yet another embodiment, the first dose of the larazotide or a derivative thereof is formulated for release in, for example, the large intestine (e.g., one or more of cecum, ascending, transverse, descending or sigmoid portions of the colon, and rectum), whereas the second dose is formulated for delayed release in, for example, another part of the large intestine (e.g., one or more of cecum, ascending, transverse, descending or sigmoid portions of the colon, and rectum). In some embodiments, the pharmaceutical composition and/or formulation releases at least one dose, at least two doses, at least three doses, at least four doses, or at least five doses of the larazotide or a derivative thereof, at different locations along the intestines, at different times, and/or at different pH.

In some embodiments, the larazotide or derivative is administered to each of the duodenum, jejunum, and the ileum. In some embodiments, the larazotide or derivative is further administered to the large intestine.

In some embodiments, compositions comprising or releasing larazotide or a derivative thereof (e.g., (d)-larazotide) are administered in a regimen of at least once per day. In some embodiments, the compositions are administered in a regimen including administration from 1 to 5 times daily, such as from 1 to 3 times daily. In some embodiments, the regimen is initiated before checkpoint inhibitor therapy, for example, at least one week prior to initiation of checkpoint inhibitor therapy, or in some embodiments, at least 2 weeks, at least 3 weeks, at least 4 weeks (about 1 month) prior to initiation of checkpoint inhibitor therapy. In these or other embodiments, the regimen is continued throughout the duration of checkpoint inhibitor therapy, and optionally for a period of time thereafter (e.g., at least one month or more after a checkpoint inhibitor therapy regimen.

In various embodiments, administration of larazotide or derivative (e.g., (d)-larazotide) increases or restores the efficacy of immune checkpoint inhibitor therapy. For example, in some embodiments, the subject having cancer was previously unresponsive to, or had become resistant to, an immune checkpoint inhibitor. In some embodiments, for example, the cancer is refractory or insufficiently responsive to an immunotherapy, such as anti-CTLA-4, anti-PD-1, or anti-PD-L1 and/or PD-L2 agent. In some embodiments, the cancer subject has progressed after or during treatment with an anti-CTLA-4, anti-PD-1, or anti-PD-L1 and/or PD-L2 agent, including for example, one or more of ipilimumab, tremelimumab, pembrolizumab and nivolumab, or shown no response to such treatment for at least about 4 weeks, or at least about 8 weeks, or at least about 12 weeks of treatment.

The cancer can be any cancer treatable by immune checkpoint inhibitor therapy, including primary cancer or a metastatic cancer. A primary cancer refers to cancer cells at an originating site that become clinically detectable, and may be a primary tumor. "Metastasis" refers to the spread of cancer from a primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant.

In some embodiments, the cancer may have an origin from any tissue. In some embodiments, the cancer may originate from skin, colon, breast, or prostate, and thus may be made up of cells that were originally skin, colon, breast, or prostate, respectively. In some embodiments, the cancer may also be a hematological malignancy, which may be lymphoma or leukemia. In some embodiments, the primary or metastatic cancer is lung cancer, breast cancer, kidney cancer, liver cancer, prostate cancer, cervical cancer, colorectal cancer, pancreatic cancer, melanoma, ovarian cancer, bone cancer, urothelial cancer, gastric cancer, head and neck cancer, glioblastoma, head and neck squamous cell carcinoma (HNSCC), non-small cell lung carcinoma (NSCLC), small cell lung cancer (SCLC), bladder cancer, prostate cancer (e.g. hormone-refractory). In some embodiments, the cancer is melanoma, colorectal cancer, or head and neck cancer.

In some embodiments, the cancer is progressive, locally advanced, or metastatic carcinoma. In some embodiments, the cancer is metastatic melanoma, and may be recurrent. In some embodiments, the metastatic melanoma is stage III or IV, and may be stage IVA, IVB, or IVC. The metastasis may be regional or distant.

In some embodiments, the solid tumor is a sarcoma or carcinoma. In some embodiments, the solid tumor is a relapsed or refractory solid tumor. In some embodiments, the relapsed or refractory solid tumor is a sarcoma or carcinoma. In some embodiments, the solid tumor is a metastasized solid tumor. In some embodiments, the metastasized solid tumor is a sarcoma or carcinoma.

In some embodiments, the cancer is a hematological cancer. In some embodiments, the hematologic cancer is a leukemia, a lymphoma, a myeloma, a non-Hodgkin's lymphoma, a Hodgkin's lymphoma, a T-cell malignancy, or a B-cell malignancy.

EXAMPLES

The following experiments evaluated the impact of larazotide immunomodulatory properties, including in combination with immune checkpoint inhibition.

The present Example shows that larazotide, and particularly (d)-larazotide, can prevent and/or restore the functional integrity of the ileal and/or colonic intestinal barrier in cancer bearers, which may also improve the clinical benefit of immune checkpoint blockade. Specifically, it was found that (d)-larazotide (referred to herein as "INN-202") has utility as an anticancer therapy—as a standalone therapy (e.g., against melanoma) and for its immunostimulating capacity in combination with the two major pillars of immunotherapy of cancer: anti-PD1 and anti-CTLA4 antibodies. It was shown that (d)-larazotide both slowed the tumor progression and enhanced the efficacy of ICB (anti-PD1+anti-CTLA4 antibodies). Furthermore, the effects of (d)-larazotide were not observed in the absence of T cells, suggesting a direct or indirect immunostimulatory property of (d)-larazotide.

1. Larazotide was Evaluated in an MCA205 Subcutaneous Model.

Figure 1B:
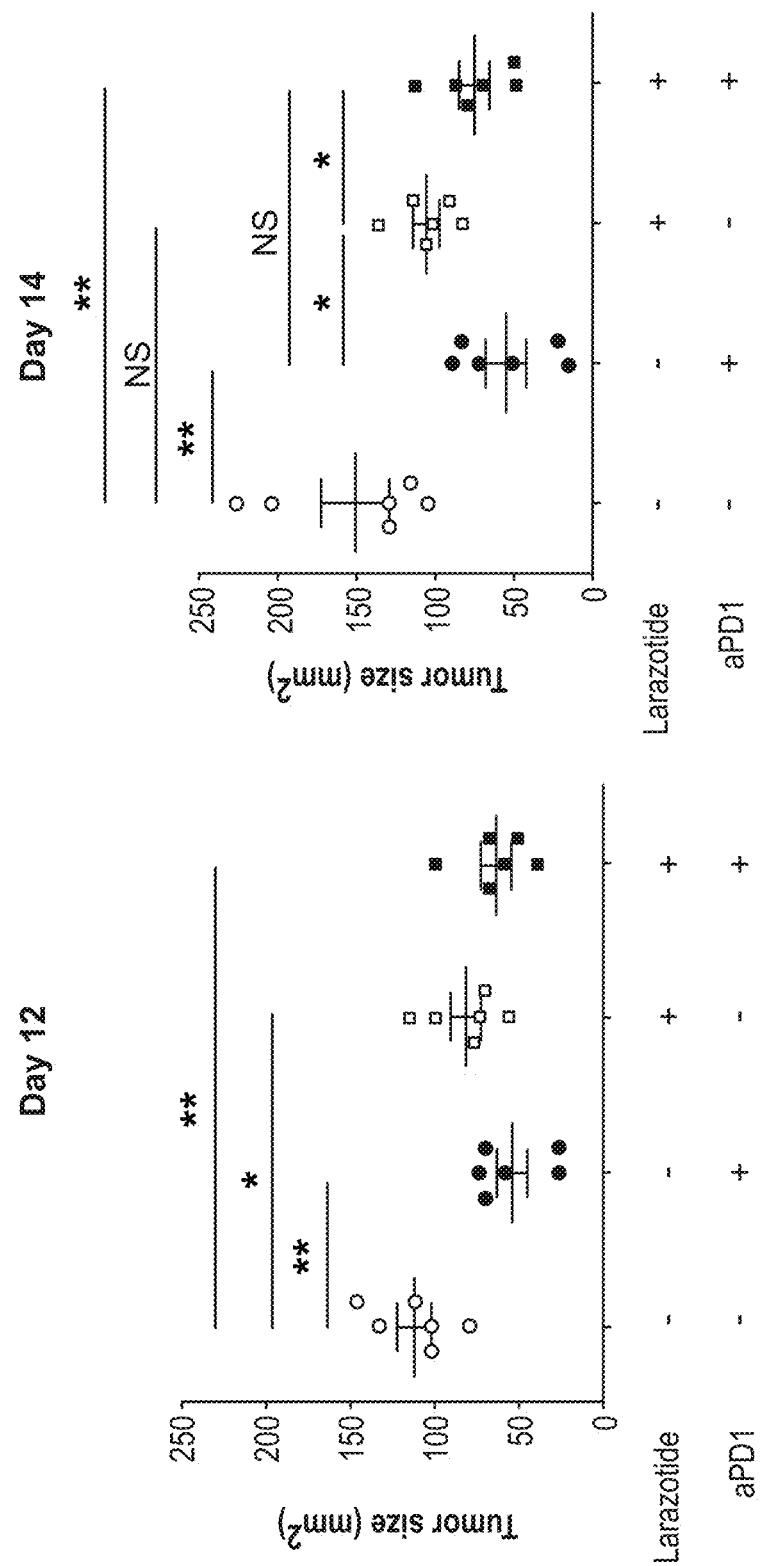
Figure 1B:
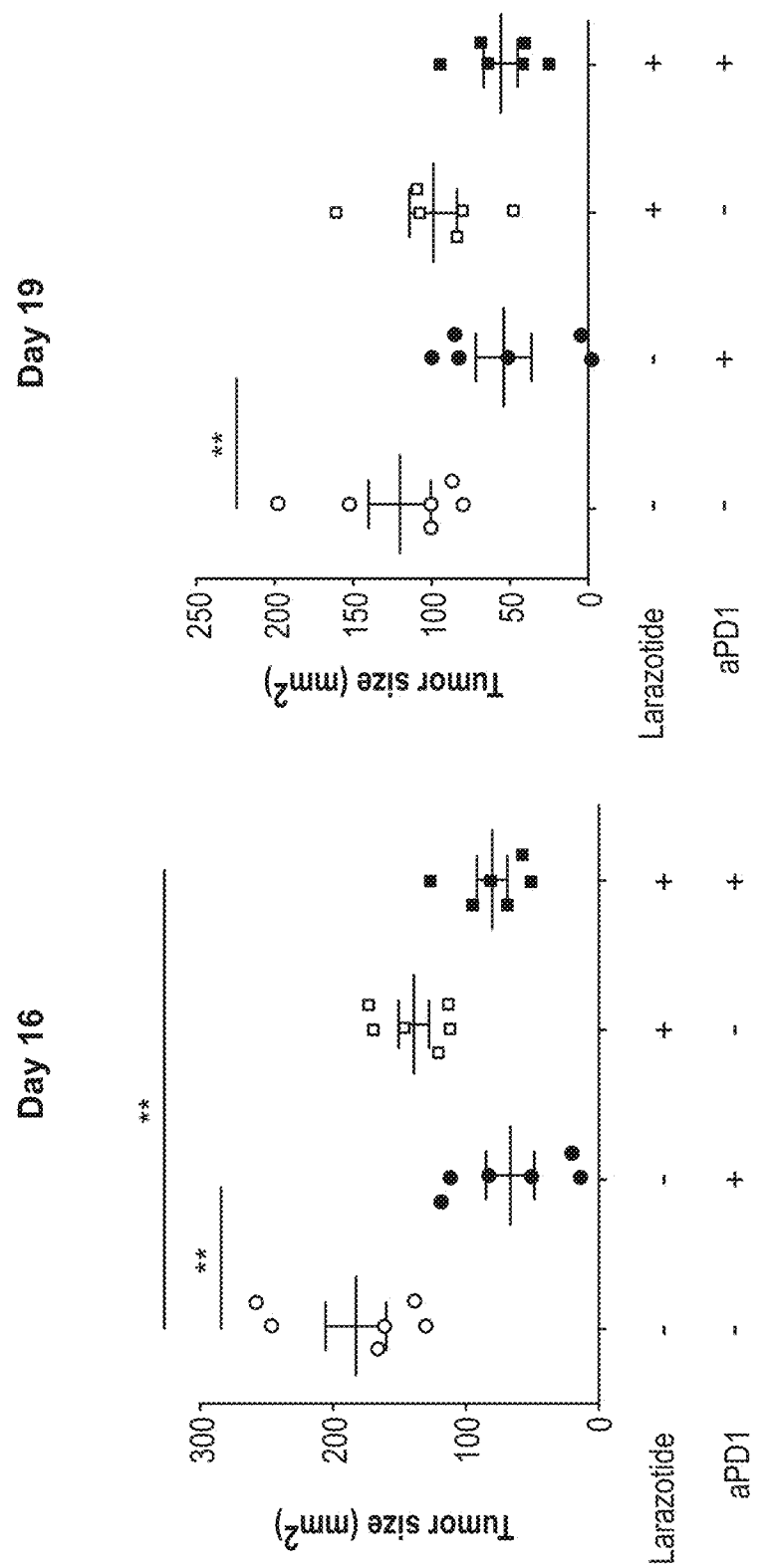
Figure 1C:
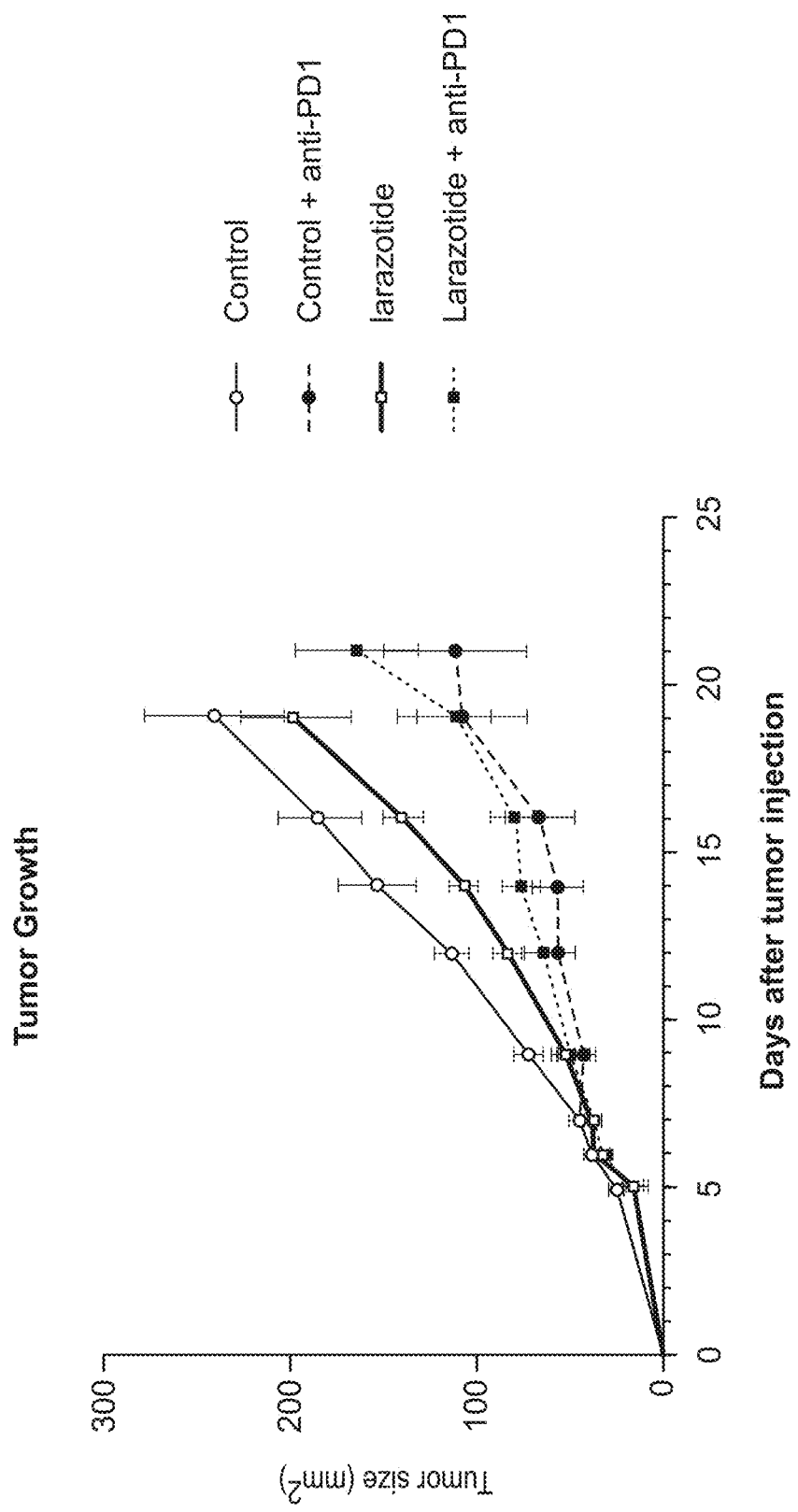

The prophylactic effect of larazotide was investigated on MCA205 tumor growth kinetics in C57BL/6 mice. Specifically, mice were injected subcutaneously with MCA205 fibrosarcoma cells and were treated two days later with larazotide by intraperitoneal injection. A decrease in tumor size was observed at day 5 that was significantly sustained until day 14 (see FIGS. 1B and 1C).

Figure 1D:
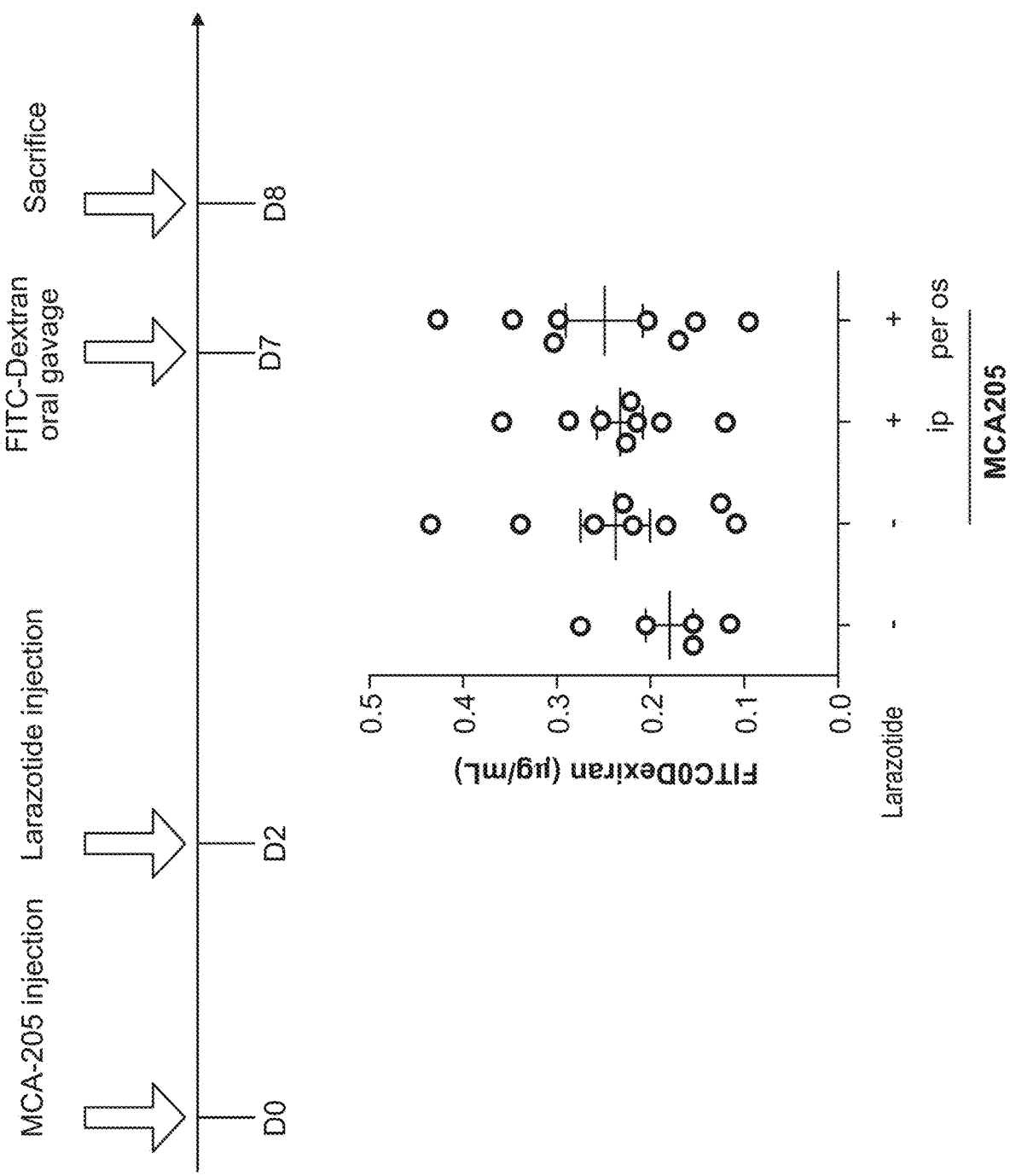

Next, the effect of larazotide in the context of anti-PD1 antibody therapy was evaluated. MCA205 tumor-bearing mice were treated with larazotide 2 days per week and with anti-PD1 antibody by intraperitoneal injection at 3 day intervals. While anti-PD1 treatment reduces MCA205 tumor progression, larazotide did not appear to enhance this effect. Intestinal permeability after MCA205 tumor inoculation was also evaluated at day 7, using the FITC Dextran assay (serum fluorescence after oral gavage of fluorescein isothiocyanate (FITC)-dextran, as previously described (see Viaud et al. Science 2013)). In this experiment, the sarcoma implantation did not significantly cause a leakage of FITC-dextran in the circulation, except in rare cases, and larazotide treatment did not modulate this effect (see FIG. 1D).

2. (d)-Larazotide was Evaluated Alone and in Combination with Anti-PD1+Anti-CTLA4 Antibodies (cICB) in a RET Melanoma Model.

Figure 2B:
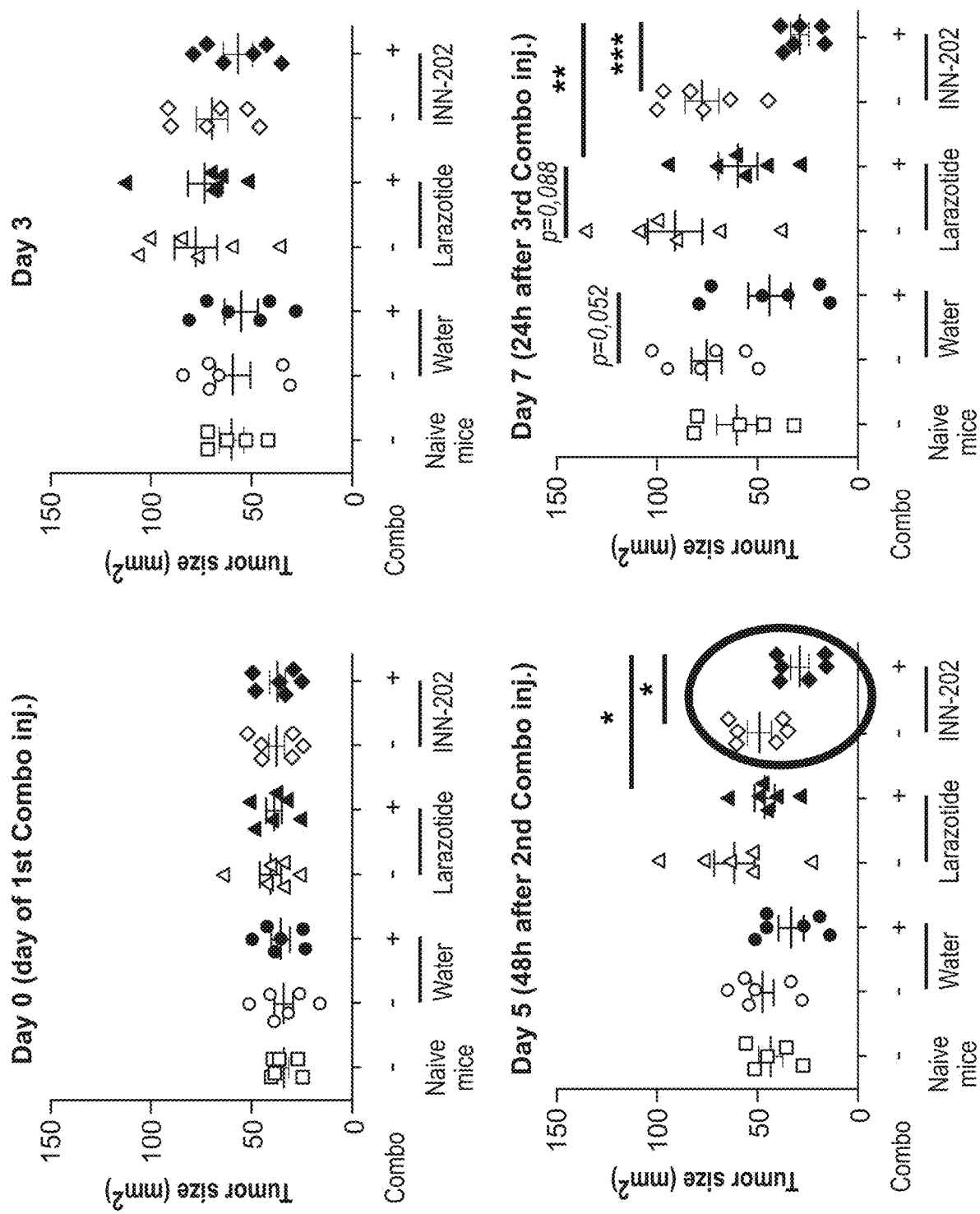
Figure 2C:
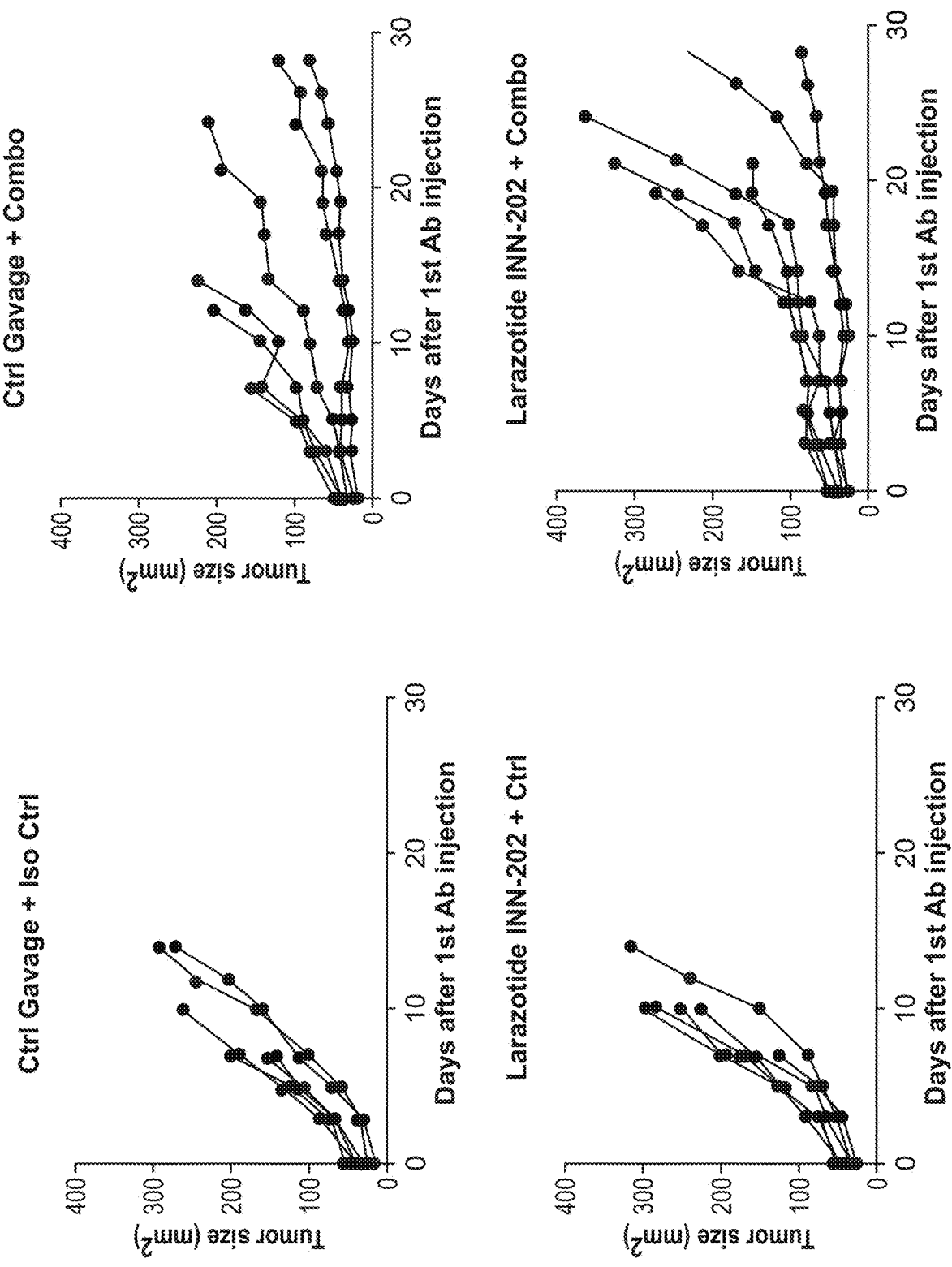
Figure 2C:
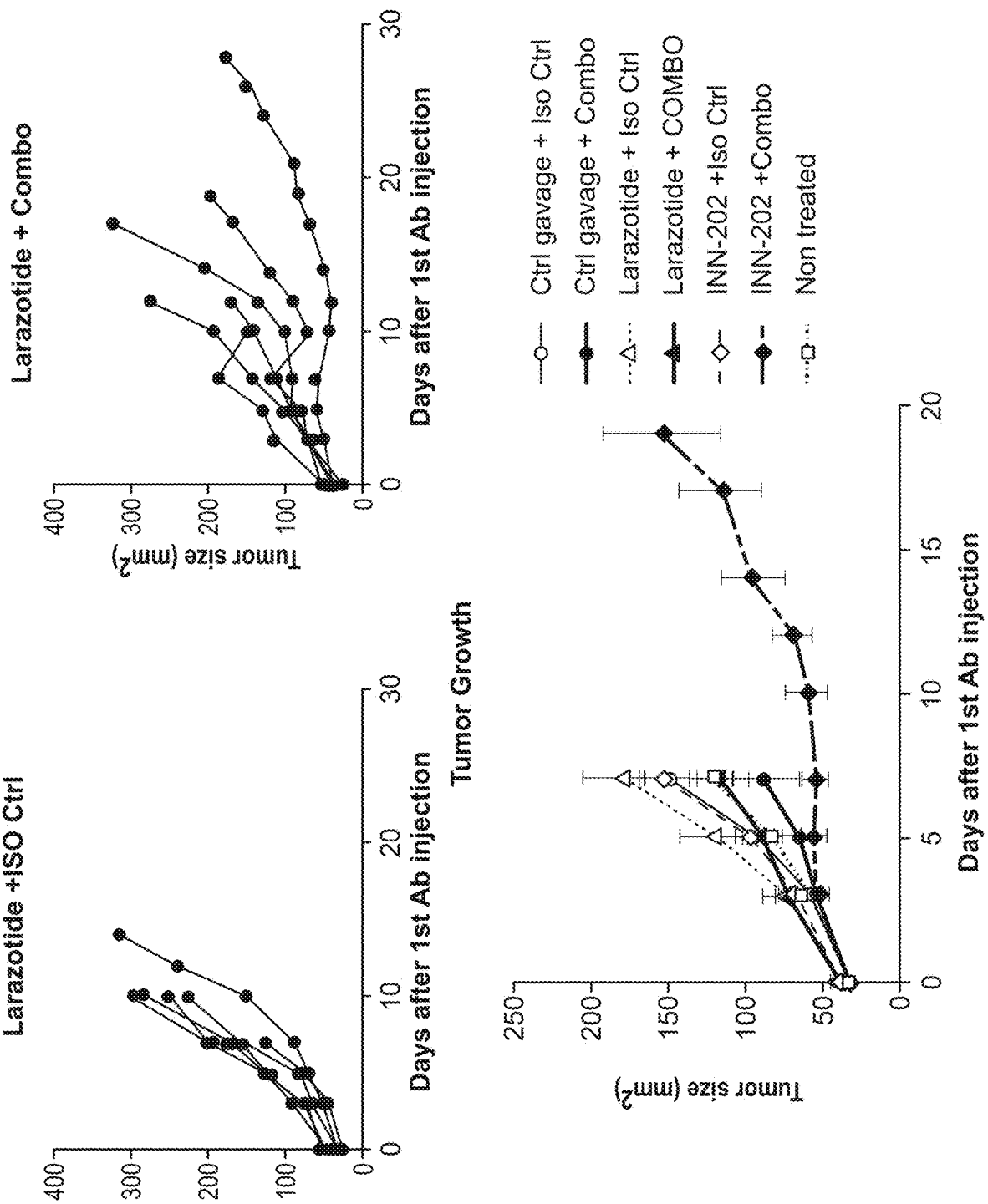

The anti-tumor efficacy of larazotide and (d)-larazotide (INN-202) was compared alone and in combination with ICB (anti-PD1+anti-CTLA4), using a RET melanoma model. Specifically, mice were subcutaneously injected with RET melanoma cells and were treated (1) with larazotide or (d)-larazotide five times a week from the day of the tumor injection and (2) with ICB (anti-PD1+anti-CTLA4) when the tumor reached 20 to 35 mm² in size. The results showed that neither larazotide nor (d)-larazotide prevented the outgrowth of RET as a standalone therapy (see FIG. 2B). Larazotide in fact tended to boost RET outgrowth within the first 10 days, as compared to naive and control mice (see FIG. 2B). However, the data shows that 48 hours after the second cICB administration, (d)-larazotide promptly and significantly decreased tumor progression compared to the control group or (d)-larazotide alone group (FIG. 2B,C). The combination of (d)-larazotide and cICB was the only group prolonging overall survival and sustained anticancer effects (FIG. 2D).

Figure 3A:
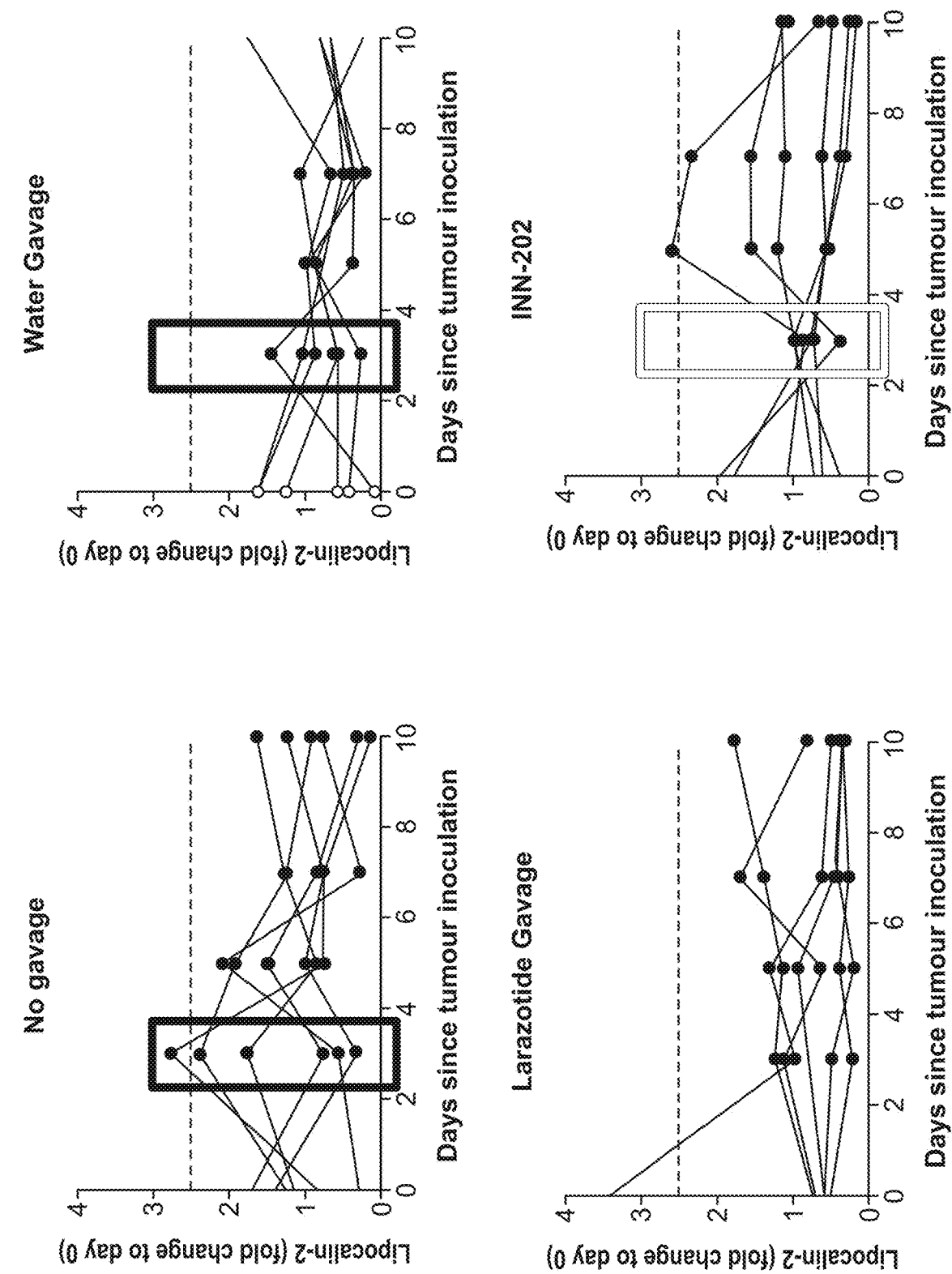
FIG. 3A-C show that oral gavage of larazotide or (d)-larazotide may induce plasma ST2 and sCD14.
Figure 3B:
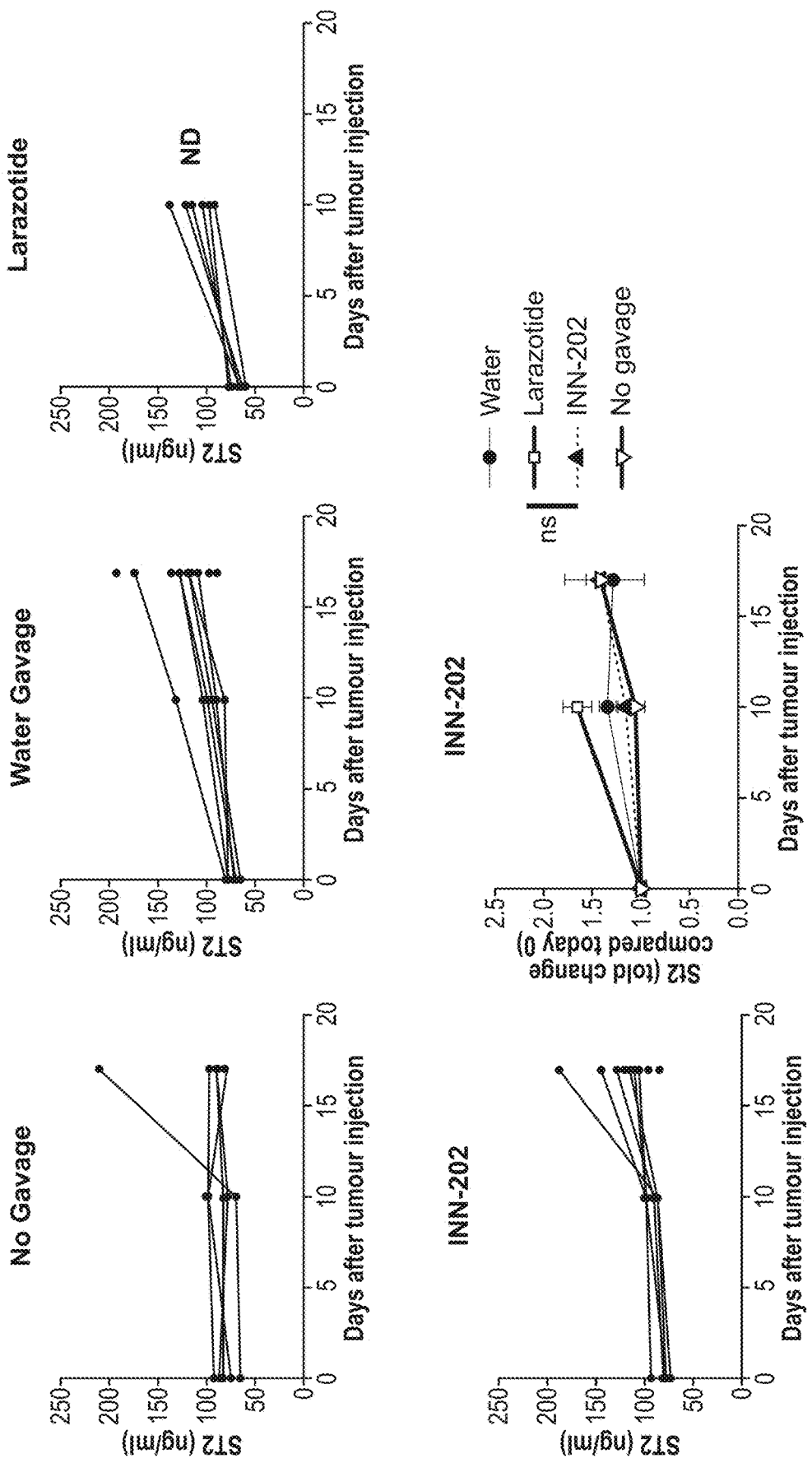
Figure 3C:
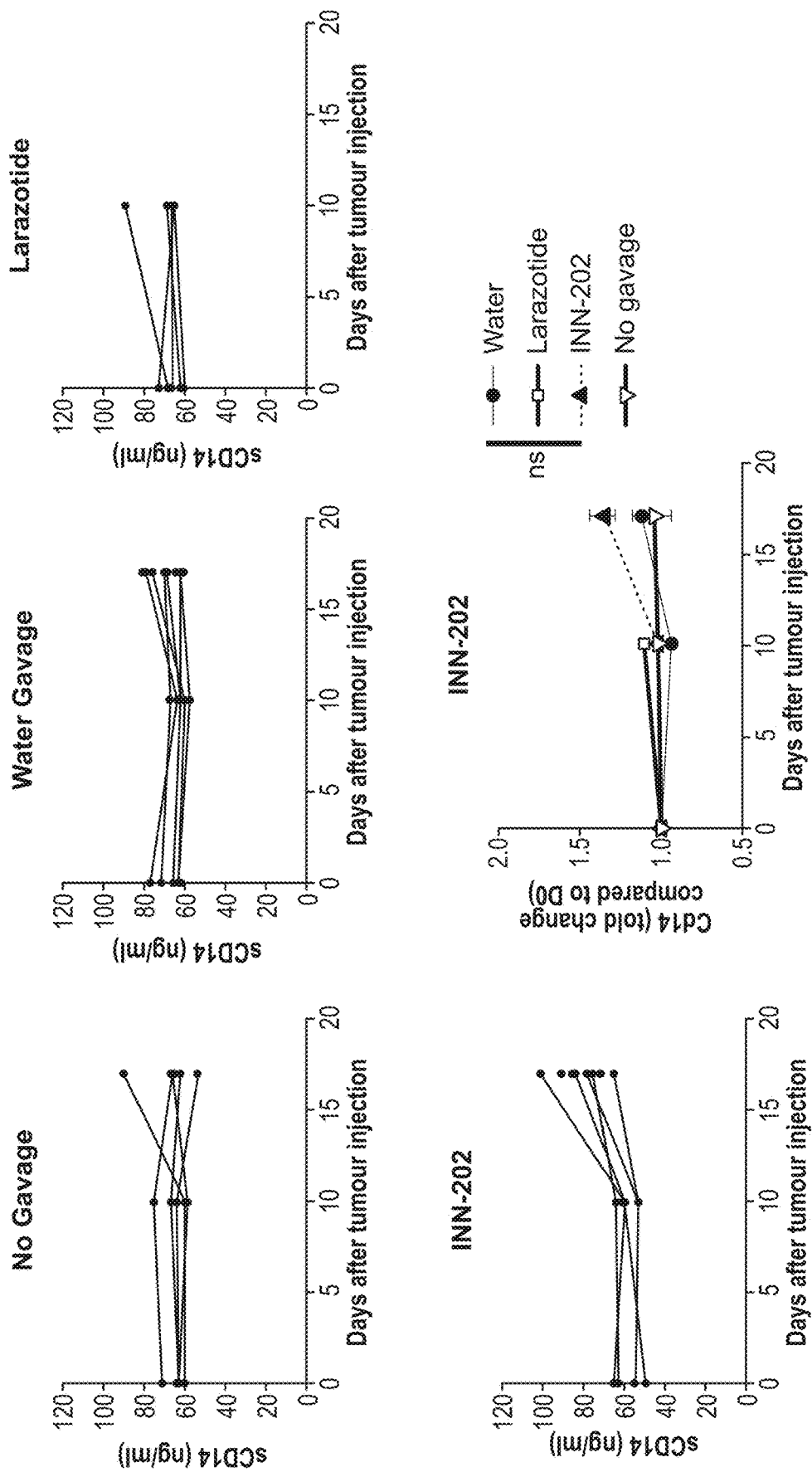

This synergistic antitumor effect was shown to be associated with a decrease in intestinal release of the lipocalin-2 in stools, a marker of intestinal inflammation. (d)-larazotide also prevented the increase of circulating soluble ST2 (s ST2), a hallmark of gut barrier damage, and may increase soluble CD14 (s CD14), which suggests some effects on microbial products translocation (see FIG. 3A-C). The experiment was reproduced three times using (d)-larazotide treatment only, which was more effective than larazotide in combination with cICB.

Figure 4A:
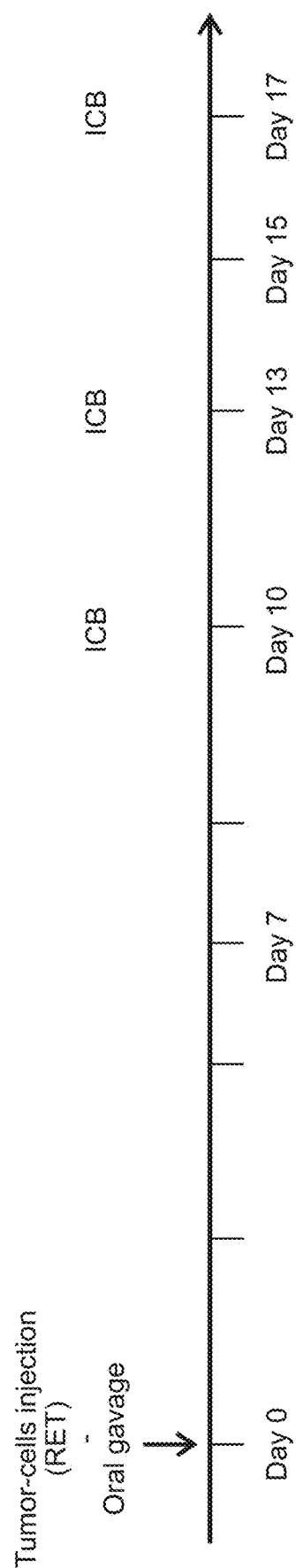
FIG. 4A-C depict pooled data showing the efficacy of (d)-larazotide (INN-202), along with ICB against the RET orthotopic melanoma.
Figure 4B:
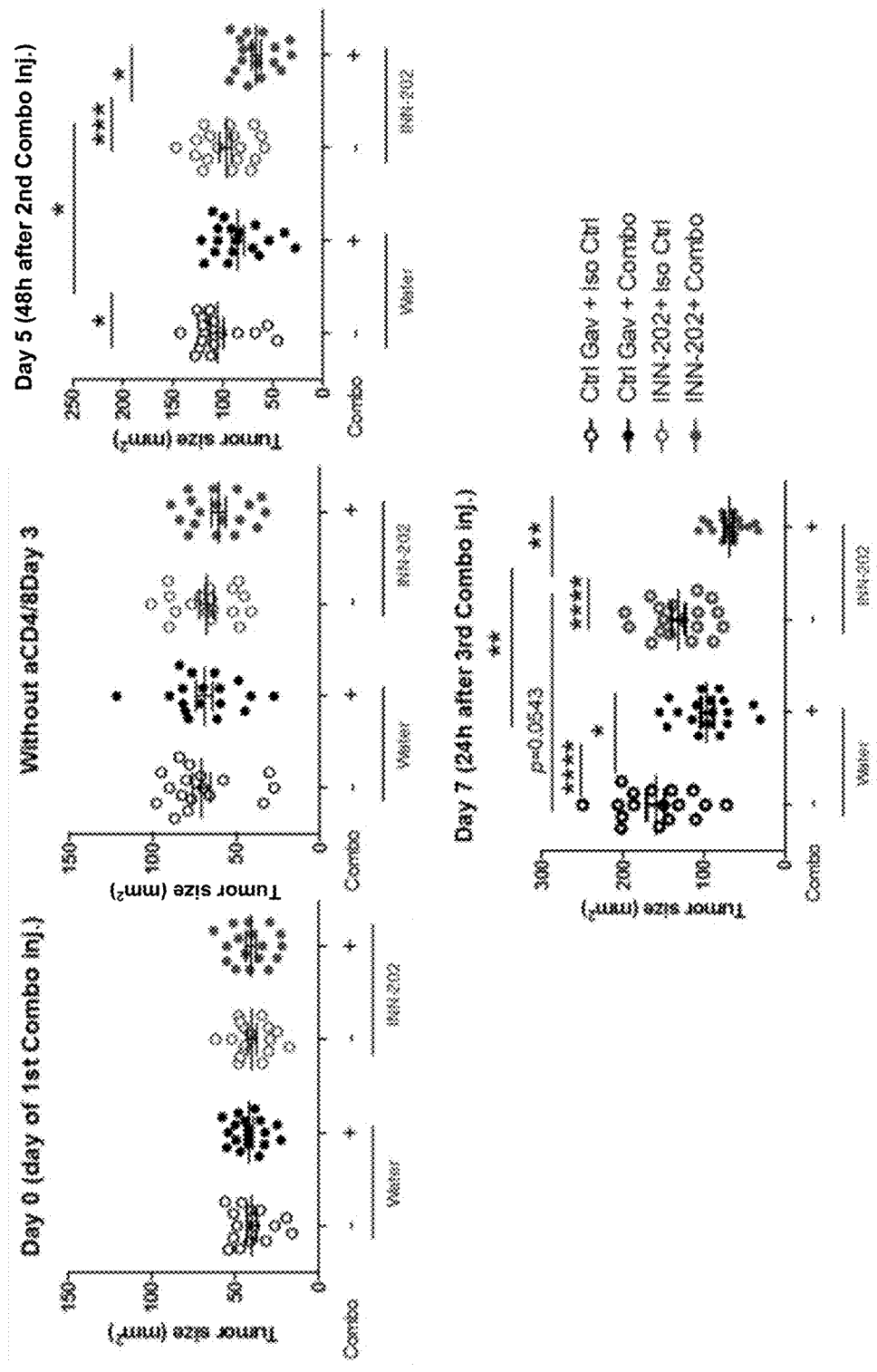
Figure 4C:
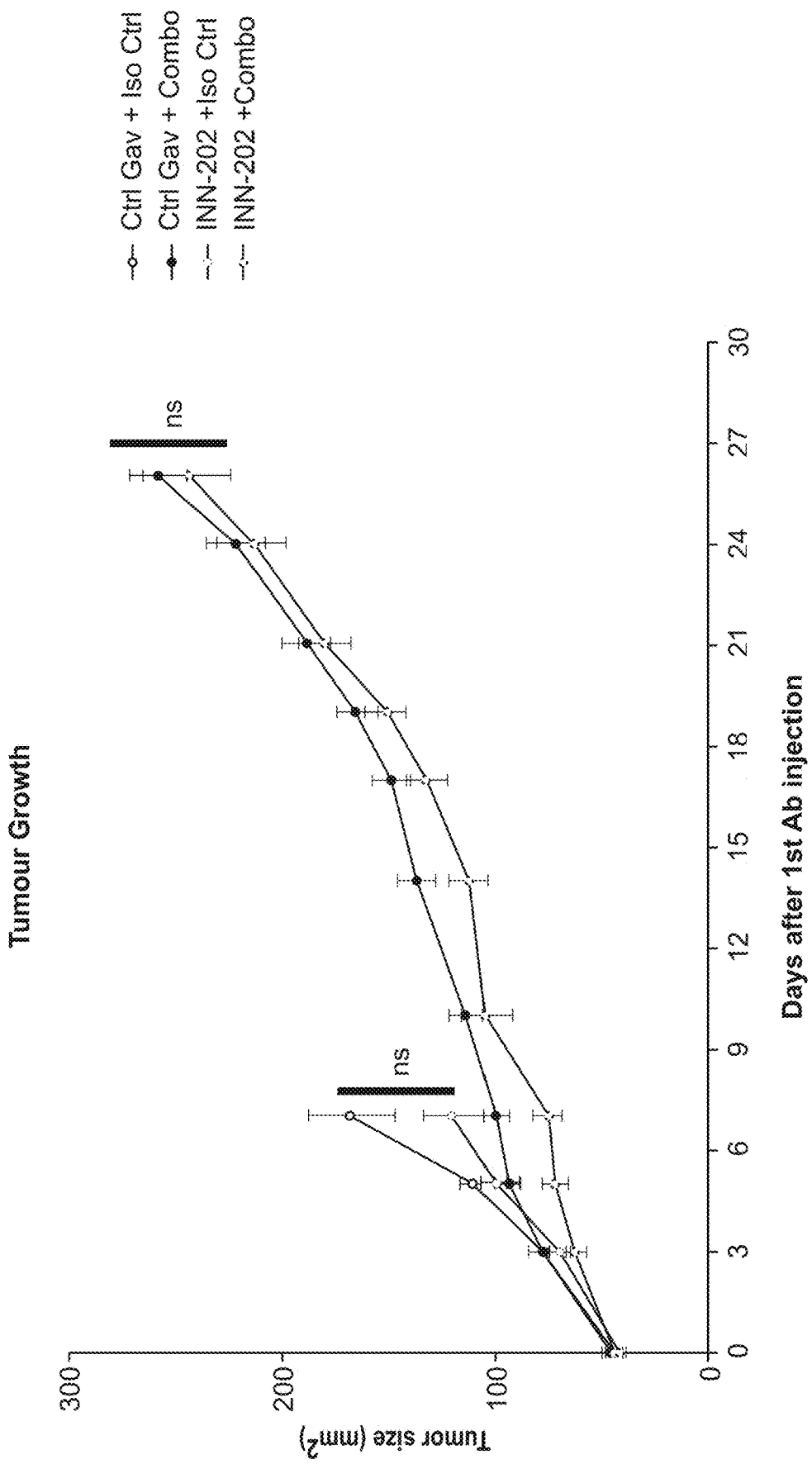

As a standalone therapy, it was shown that (d)-larazotide reduced tumor progression with a long lasting protection when compared with the control group, albeit with less efficacy than cICB alone. Moreover, oral gavage of (d)-larazotide significantly improved the efficacy of cICB (anti-PD1+anti CTLA4 antibodies) and prolonged survival. FIG. 4(A-C) shows the concatenated data pooling three independent experiments gathering 6 mice/group for each experiment. Of note, the animals appeared healthy with no overt signs of toxicity.

3. Combination Therapy of (d)-Larazotide and cICB was Evaluated for T Cell-Dependent Efficacy.

Figure 5A:
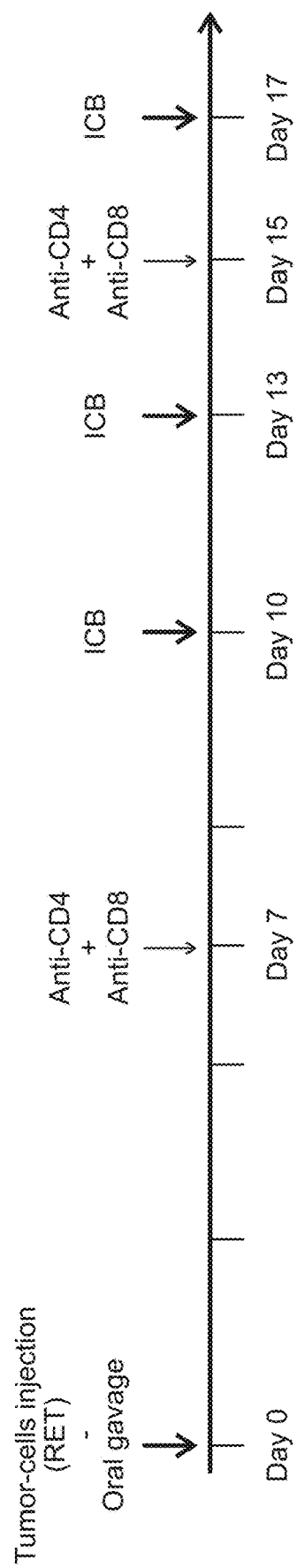
Figure 5C:
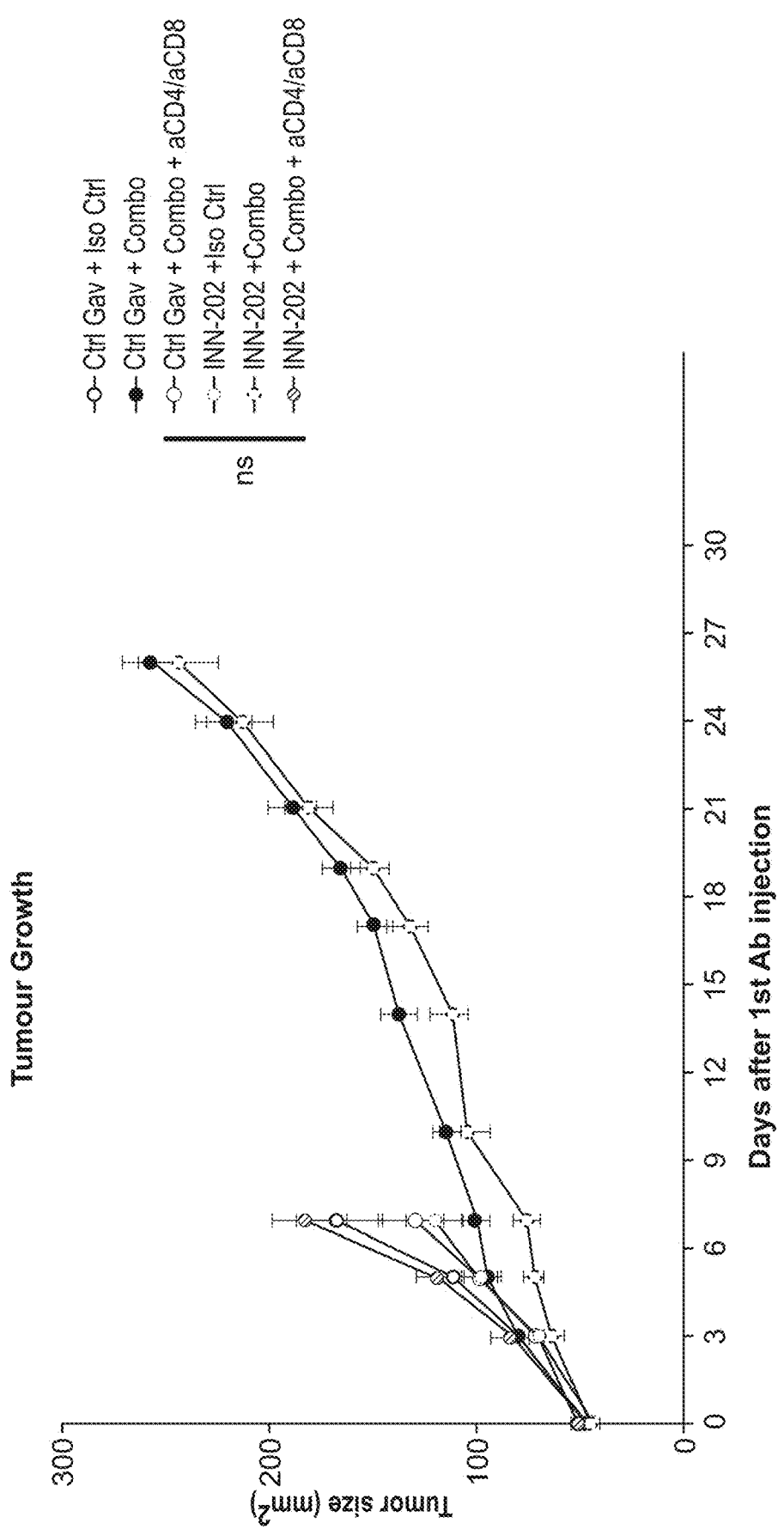

Because tumor outgrowth is mainly controlled by CD4+ and CD8+ T cells, the role of these cell populations was investigated in relation to (d)-larazotide efficacy. It was shown that anti-CD8 and anti-CD4 mAb treatment completely abrogated the therapeutic effects of combined immunotherapy in both water-treated and (d)-larazotide-treated mice. These data demonstrate a role of CD4/CD8 T cells response in the effect of ICB/(d)-larazotide mAb treatment (see FIG. 5A-C).

What is claimed is:

1. A method for treating cancer in a patient undergoing an immune checkpoint inhibitor therapy targeting immune checkpoints selected from PD-1, PD-L1, and CTLA-4, the method comprising administering to the gastrointestinal tract of said patient an oral dosage composition comprising an amount effective to potentiate the immune checkpoint inhibitor therapy against the cancer of a peptide having the amino acid sequence of SEQ ID NO: 1, or a pharmaceutically acceptable salt thereof, with the proviso that all non-glycine amino acid residues of SEQ ID NO: 1 are in (d) form.

2. The method of claim 1, wherein the immune checkpoint inhibitor is selected from ipilimumab, tremelimumab, pembrolizumab and nivolumab.

3. The method of claim 1, wherein the patient showed no response or only partial response to prior treatment with an immune checkpoint inhibitor therapy.

4. The method of claim 3, wherein the prior immune checkpoint inhibitor therapy was a PD-1 blockade therapy.

5. The method of claim 1, wherein the peptide is administered in a pharmaceutical composition that does not substantially release peptide in the stomach, and releases the peptide in the small intestine and/or large intestine.

6. The method of claim 5, wherein the peptide is released in one or more of the duodenum, jejunum, and the ileum.

7. The method of claim 5, wherein the peptide is released in the large intestine.

8. The method of claim 7, wherein the peptide is released in the colon.

9. The method of claim 5, wherein the peptide is administered in a sustained release formulation that releases peptide in the gastrointestinal tract for at least 2 hours.

10. The method of claim 9, wherein the sustained release formulation releases peptide in the gastrointestinal tract for at least 3 hours.

11. The method of claim 1, wherein the peptide is administered from 1 to 3 times per day.

12. The method of claim 11, wherein the peptide is administered throughout the immune checkpoint inhibitor therapy.

13. The method of claim 12, wherein the peptide is further administered after the immune checkpoint inhibitor therapy.

14. The method of claim 11, wherein the peptide is additionally administered for at least one week prior to initiation of the immune checkpoint inhibitor therapy.

15. The method of claim 14, wherein the peptide is administered throughout the duration of the immune checkpoint inhibitor therapy.

16. The method of claim 15, wherein the peptide is further administered after the checkpoint inhibitor therapy.

17. The method if claim 1, wherein the patient has primary cancer.

18. The method of claim 1, wherein the patient has metastatic cancer.

19. The method of claim 18, wherein the patient has metastatic melanoma.

20. The method of claim 1, wherein the patient has colorectal cancer.

21. The method of claim 1, wherein the patient has sarcoma or carcinoma.

22. The method of claim 1, wherein the patient has a hematological cancer.

23. The method of claim 22, wherein the patient has a leukemia, myeloma, or lymphoma.

* * * * *

SEQUENCE LISTING

```
<160> NUMBER OF SEQ ID NOS: 24

<210> SEQ ID NO 1
<211> LENGTH: 8
<212> TYPE: PRT
<213> ORGANISM: Artificial Sequence
<220> FEATURE:
<223> OTHER INFORMATION: Synthetic polymer

<400> SEQUENCE: 1

Gly Gly Val Leu Val Gln Pro Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic polymer

<400> SEQUENCE: 2

Gly Arg Val Cys Val Gln Pro Gly
1               5
```

-continued

```
<210> SEQ ID NO 3
<211> LENGTH: 8
<212> TYPE: PRT
<213> ORGANISM: Artificial Sequence
<220> FEATURE:
<223> OTHER INFORMATION: Synthetic polymer

<400> SEQUENCE: 3

Gly Arg Val Cys Val Gln Asp Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic polymer

<400> SEQUENCE: 4

Gly Arg Val Leu Val Gln Pro Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic polymer

<400> SEQUENCE: 5

Gly Arg Val Leu Val Gln Asp Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic polymer

<400> SEQUENCE: 6

Gly Arg Leu Cys Val Gln Pro Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic polymer

<400> SEQUENCE: 7

Gly Arg Leu Cys Val Gln Asp Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic polymer

<400> SEQUENCE: 8

Gly Arg Leu Leu Val Gln Pro Gly
1               5

<210> SEQ ID NO 9
```

```
<211> LENGTH: 8
<212> TYPE: PRT
<213> ORGANISM: Artificial Sequence
<220> FEATURE:
<223> OTHER INFORMATION: Synthetic polymer

<400> SEQUENCE: 9

Gly Arg Leu Leu Val Gln Asp Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic polymer

<400> SEQUENCE: 10

Gly Arg Gly Cys Val Gln Pro Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic polymer

<400> SEQUENCE: 11

Gly Arg Gly Cys Val Gln Asp Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic polymer

<400> SEQUENCE: 12

Gly Arg Gly Leu Val Gln Pro Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic polymer

<400> SEQUENCE: 13

Gly Arg Gly Leu Val Gln Asp Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic polymer

<400> SEQUENCE: 14

Gly Gly Val Cys Val Gln Pro Gly
1               5

<210> SEQ ID NO 15
<211> LENGTH: 8
```

```
<212> TYPE: PRT
<213> ORGANISM: Artificial Sequence
<220> FEATURE:
<223> OTHER INFORMATION: Synthetic polymer

<400> SEQUENCE: 15

Gly Gly Val Cys Val Gln Asp Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic polymer

<400> SEQUENCE: 16

Gly Gly Val Leu Val Gln Asp Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic polymer

<400> SEQUENCE: 17

Gly Gly Leu Cys Val Gln Pro Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic polymer

<400> SEQUENCE: 18

Gly Gly Leu Cys Val Gln Asp Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic polymer

<400> SEQUENCE: 19

Gly Gly Leu Leu Val Gln Pro Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic polymer

<400> SEQUENCE: 20

Gly Gly Leu Leu Val Gln Asp Gly
1               5

<210> SEQ ID NO 21
<211> LENGTH: 8
<212> TYPE: PRT
```

```
<213> ORGANISM: Artificial Sequence
<220> FEATURE:
<223> OTHER INFORMATION: Synthetic polymer

<400> SEQUENCE: 21

Gly Gly Gly Cys Val Gln Pro Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic polymer

<400> SEQUENCE: 22

Gly Gly Gly Cys Val Gln Asp Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic polymer

<400> SEQUENCE: 23

Gly Gly Gly Leu Val Gln Pro Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic polymer

<400> SEQUENCE: 24

Gly Gly Gly Leu Val Gln Asp Gly
1               5
```